United States Patent
Deshaies et al.

(10) Patent No.: US 11,590,034 B2
(45) Date of Patent: Feb. 28, 2023

(54) REUSABLE ABSORBENT ACCESSORIES AND ASSOCIATED METHODS

(71) Applicant: Knix Wear Inc., Toronto (CA)

(72) Inventors: Lyne Deshaies, Toronto (CA); Talia Greenberg, Toronto (CA); Joanna Griffiths, Toronto (CA); Steven Hudson, Toronto (CA); Jeremy Jiang, Kunshan (CN); Julie Power, Toronto (CA); Linda Kritikos, Toronto (CA)

(73) Assignee: Knix Wear Inc., Ontario (CA)

( * ) Notice: Subject to any disclaimer, the term of this patent is extended or adjusted under 35 U.S.C. 154(b) by 0 days.

(21) Appl. No.: 17/718,096

(22) Filed: Apr. 11, 2022

(65) Prior Publication Data

US 2023/0012670 A1    Jan. 19, 2023

Related U.S. Application Data

(60) Provisional application No. 63/273,444, filed on Oct. 29, 2021, provisional application No. 63/219,763, filed on Jul. 8, 2021.

(51) Int. Cl.
*A61F 13/15*    (2006.01)
*A61F 13/505*    (2006.01)
(Continued)

(52) U.S. Cl.
CPC ...... *A61F 13/505* (2013.01); *A61F 13/15739* (2013.01); *A61F 13/539* (2013.01);
(Continued)

(58) Field of Classification Search
CPC .............. A61F 13/505; A61F 13/15739; A61F 13/539; A61F 13/5611; A61F 2013/530897; A61F 2013/53908; A61F 2013/5055
See application file for complete search history.

(56) References Cited

U.S. PATENT DOCUMENTS 2,985,170 A    5/1961    Title
3,489,149 A    1/1970    Larson
(Continued)

FOREIGN PATENT DOCUMENTS

AU    2006209375 A1    10/2006
AU    2014218471 B2    10/2016
(Continued)

OTHER PUBLICATIONS

English-language machine translation of Japan Patent Application Publication No. JP2005154922, Jun. 16, 2005.
(Continued)

*Primary Examiner* — Jacqueline F Stephens
(74) *Attorney, Agent, or Firm* — Kolitch Romano Dascenzo Gates LLC

(57) ABSTRACT

Reusable absorbent accessories are configured to be worn by a wearer, are configured to be washed and re-worn numerous times, and comprise adhesive bonds within a bonded region; a base; a moisture capture assembly bonded to the base within the bonded region and comprising a moisture retention portion configured to absorb and retain moisture from the wearer, and an anti-leak portion configured to restrict moisture from exiting the moisture retention portion and positioned toward the assembly exterior side of the moisture capture assembly relative to the moisture retention portion.

20 Claims, 7 Drawing Sheets

(51) Int. Cl.
*A61F 13/539* (2006.01)
*A61F 13/56* (2006.01)
*A61F 13/53* (2006.01)

(52) U.S. Cl.
CPC .................. *A61F 13/5611* (2013.01); *A61F 2013/530897* (2013.01); *A61F 2013/53908* (2013.01)

(56) References Cited

U.S. PATENT DOCUMENTS

| | | | |
|---|---|---|---|
| 3,608,551 A | 9/1971 | Saburo | |
| 3,687,141 A | 8/1972 | Matsuda | |
| 4,044,769 A | 8/1977 | Papajohn | |
| 4,355,425 A | 10/1982 | Jones et al. | |
| 4,560,381 A | 12/1985 | Southwell | |
| 4,781,962 A | 11/1988 | Zamarripa et al. | |
| 4,847,134 A | 7/1989 | Fahrenkrug et al. | |
| 5,151,092 A | 9/1992 | Buell et al. | |
| 5,167,897 A | 12/1992 | Weber et al. | |
| 5,217,782 A | 6/1993 | Moretz et al. | |
| 5,224,941 A | 7/1993 | Simmons | |
| 5,308,346 A | 5/1994 | Sneller et al. | |
| 5,342,338 A | 8/1994 | Roe | |
| 5,360,420 A | 11/1994 | Cook et al. | |
| 5,368,910 A | 11/1994 | Langdon | |
| 5,411,498 A | 5/1995 | Fahrenkrug et al. | |
| 5,449,352 A | 9/1995 | Nishino et al. | |
| 5,500,270 A | 3/1996 | Langdon et al. | |
| 5,507,895 A | 4/1996 | Suekane | |
| 5,518,801 A | 5/1996 | Chappell et al. | |
| 5,665,452 A | 9/1997 | Langdon et al. | |
| 5,677,028 A | 10/1997 | Ravella | |
| 5,693,169 A | 12/1997 | Langdon et al. | |
| 5,707,364 A * | 1/1998 | Coates .................. A61F 13/622 |
| | | | 604/385.01 |
| H1732 H | 6/1998 | Johnson | |
| H1746 H | 8/1998 | Carrier et al. | |
| 5,851,204 A | 12/1998 | Mizutani | |
| 5,855,573 A | 1/1999 | Johansson | |
| 5,879,487 A | 3/1999 | Ravella | |
| 5,899,895 A | 5/1999 | Robles et al. | |
| 6,117,523 A | 9/2000 | Sugahara | |
| 6,120,487 A | 9/2000 | Ashton | |
| 6,174,303 B1 | 1/2001 | Suprise et al. | |
| 6,231,554 B1 | 5/2001 | Menard | |
| 6,240,569 B1 | 6/2001 | Van Gompel et al. | |
| 6,355,330 B1 | 3/2002 | Koslow et al. | |
| 6,381,994 B1 | 5/2002 | Lee | |
| 6,610,901 B2 | 8/2003 | Mcmahon-Ayerst et al. | |
| 6,622,312 B2 | 9/2003 | Rabinowicz | |
| 6,861,520 B1 | 3/2005 | Todd et al. | |
| 7,008,887 B2 | 3/2006 | Rearick et al. | |
| 7,083,604 B2 | 8/2006 | Sakaguchi | |
| 7,156,828 B2 | 1/2007 | Ostrow | |
| RE39,919 E | 11/2007 | Dodge, II et al. | |
| 7,322,966 B1 | 1/2008 | Deerin | |
| 7,951,128 B1 | 5/2011 | Lewis | |
| 8,058,343 B2 | 11/2011 | Liu et al. | |
| 8,117,675 B2 | 2/2012 | Strange et al. | |
| 8,460,265 B1 | 6/2013 | Calender | |
| D716,020 S | 10/2014 | Dunbar et al. | |
| 10,226,388 B2 | 3/2019 | Nelson | |
| 10,335,325 B2 | 7/2019 | Sheldon et al. | |
| 10,441,479 B2 | 10/2019 | Griffiths | |
| 10,441,480 B2 | 10/2019 | Griffiths | |
| 10,765,564 B2 | 9/2020 | Lee et al. | |
| 10,905,596 B2 | 2/2021 | Sina et al. | |
| 11,331,229 B2 | 5/2022 | Lee et al. | |
| 2001/0031957 A1 | 10/2001 | Prestley et al. | |
| 2002/0177829 A1 | 11/2002 | Fell et al. | |
| 2003/0004488 A1 | 1/2003 | Ashton et al. | |
| 2003/0124927 A1 | 7/2003 | Waldroup et al. | |
| 2003/0143376 A1 | 7/2003 | Toyoshima et al. | |
| 2004/0229008 A1 | 11/2004 | Hoying | |
| 2004/0236298 A1 * | 11/2004 | Coates .................. A61F 13/476 |
| | | | 604/385.04 |
| 2004/0265533 A1 | 12/2004 | Hoying et al. | |
| 2005/0055002 A1 | 3/2005 | Whitelaw et al. | |
| 2005/0090790 A1 | 4/2005 | Veith | |
| 2005/0131365 A1 | 6/2005 | Sakaguchi | |
| 2006/0070163 A1 | 4/2006 | Beck et al. | |
| 2008/0108962 A1 | 5/2008 | Furuta et al. | |
| 2008/0110775 A1 | 5/2008 | Beck et al. | |
| 2008/0275415 A1 | 11/2008 | Wheeler et al. | |
| 2008/0276352 A1 | 11/2008 | Strange et al. | |
| 2009/0240224 A1 | 9/2009 | Underhill et al. | |
| 2009/0247977 A1 | 10/2009 | Takeuchi et al. | |
| 2010/0179499 A1 * | 7/2010 | Roe .................. A61F 13/5633 |
| | | | 604/385.25 |
| 2010/0222759 A1 | 9/2010 | Hammons et al. | |
| 2010/0249736 A1 | 9/2010 | Png et al. | |
| 2011/0048077 A1 | 3/2011 | Warren et al. | |
| 2011/0224639 A1 | 9/2011 | Venable | |
| 2013/0006209 A1 * | 1/2013 | Ruiz .................. A61F 13/68 |
| | | | 604/385.14 |
| 2013/0072888 A1 | 3/2013 | Zorin | |
| 2014/0039432 A1 | 2/2014 | Dunbar et al. | |
| 2014/0378935 A1 | 12/2014 | Arayama et al. | |
| 2020/0000649 A1 | 1/2020 | Griffiths | |
| 2020/0222256 A1 | 7/2020 | Chong | |
| 2022/0117790 A1 | 4/2022 | Locke et al. | |
| 2022/0117792 A1 | 4/2022 | Bradford | |
| 2022/0133544 A1 | 5/2022 | Turton et al. | |

FOREIGN PATENT DOCUMENTS

| | | |
|---|---|---|
| CA | 2126280 | 12/1994 |
| CA | 2126281 | 12/1994 |
| CA | 2152135 | 12/1995 |
| EP | 1370161 | 5/2006 |
| JP | 2005154922 | 6/2005 |
| JP | 2005154924 | 6/2005 |
| KR | 20070018490 | 2/2007 |
| KR | 100694187 | 3/2007 |
| WO | WO 1997046198 | 12/1997 |
| WO | WO 2006036841 | 4/2006 |

OTHER PUBLICATIONS

English-language machine translation of Japan Patent Application Publication No. JP2005154924, Jun. 16, 2005.

English-language machine translation of Korea Patent No. KR100694187, Mar. 6, 2007.

English-language machine translation of Korea Patent Application Publication No. KR20070018490, Feb. 14, 2007.

"Bemis SewFree" webpage (www.bemisheatseal.com/Sewfree.htm), 2 pages, available at least as early as Aug. 4, 2001, retrieved from Internet Archive Wayback Machine (https://web.archive.org/web/20010804041402/http://www.bemisheatseal.com:%2080/Sewfree.htm) on Jan. 29, 2021.

Lo, T.Y., "Techtextil/Avantex 2005 (2)" *Textile Asia*, 2005, pp. 26-27.

Isaacs, Mac, "Seamless: Eliminating Stitches—More Than a Buzzword," *AATCC Review*, Nov. 2005, pp. 16-19.

Swantko, Kathlyn, "Forming A New Bond," *FabricTrends: A GearTrends Supplement*, 2004, pp. 12-14.

Bemis Associates, *Sewfree Adhesive Films for Intimate Apparel*, 2013, 8 pages.

Photographs of Adidas Techfit Period-Proof Biker Short Tights, ordered Jun. 24, 2021.

Photographs Lilova Seamless High Waist, ordered Oct. 12, 2021.

Photographs Lilova Swimwear One-Piece Classic, ordered Oct. 12, 2021.

Photographs of Modibodi Seamfree Bikini Moderate-Heavy, ordered Feb. 9, 2022.

Photographs of Proof Leakproof Hipster Underwear, ordered Aug. 7, 2020.

Photographs of Pure Rosy Banded Brief—Jam, ordered Oct. 12, 2021.

(56) References Cited

OTHER PUBLICATIONS

Photographs of Ruby /Love Period Underwear Bikini—Pretty In Pink, ordered May 6, 2021.
Photographs of SPEAX by Thinx Hiphugger Women's Underwear—Leakproof, Breathable—M—Beige, ordered Feb. 7, 2020.
Photographs of TomboyX Leakproof Bikini—Plum, ordered Nov. 10, 2020.

* cited by examiner

REUSABLE ABSORBENT ACCESSORIES AND ASSOCIATED METHODS

RELATED APPLICATIONS

This application claims benefit of U.S. Provisional Patent Application Nos. 63/219,763 and 63/273,444, filed on Jul. 8, 2021 and Oct. 29, 2021, respectively, the complete disclosures of which are incorporated herein by reference.

FIELD

The present disclosure relates to reusable absorbent accessories and associated methods.

BACKGROUND

Absorbent accessories and other wearable accessories that are configured to be worn adjacent to a wearer's crotch often exhibit moisture-absorbing properties, such as to absorb and/or retain menstrual fluids and/or urine produced by the user. In particular, it generally is desirable that such absorbent accessories absorb and retain such fluids in a discreet and leak-proof manner, such as to hide such fluids from view and/or to enhance the wearer's comfort. However, many such absorbent accessories include absorbent regions that are bulky and thus uncomfortable and/or difficult to conceal. Moreover, many such absorbent accessories utilize stitching to attach the absorbent regions to the remainder of the absorbent accessory, increasing the potential for leakage through the stitching perforations and/or producing bulky seams at the expense of the wearer's comfort and the discreetness of the reusable absorbent accessory. Additionally, many such absorbent accessories are configured to be disposed after a single use.

SUMMARY

Reusable absorbent accessories with moisture capture assemblies and associated methods are disclosed herein. A reusable absorbent accessory configured to be worn by a wearer includes a bonded region, a reusable absorbent accessory base, and a moisture capture assembly bonded to the reusable absorbent accessory base within the bonded region. The moisture capture assembly includes an assembly interior side that faces the wearer when the reusable absorbent accessory is worn by the wearer and an assembly exterior side that faces away from the wearer when the reusable absorbent accessory is worn by the wearer. The moisture capture assembly further includes a moisture retention portion configured to absorb and retain moisture from the wearer and an anti-leak portion configured to restrict moisture from exiting the moisture retention portion. The moisture capture assembly is bonded to the reusable absorbent accessory base with a plurality of adhesive bonds formed within the bonded region. The plurality of adhesive bonds includes an internal peripheral bond positioned on an interior side of the moisture capture assembly as well as an external peripheral bond positioned on an exterior side of the moisture capture assembly.

DESCRIPTION

Figure 1:
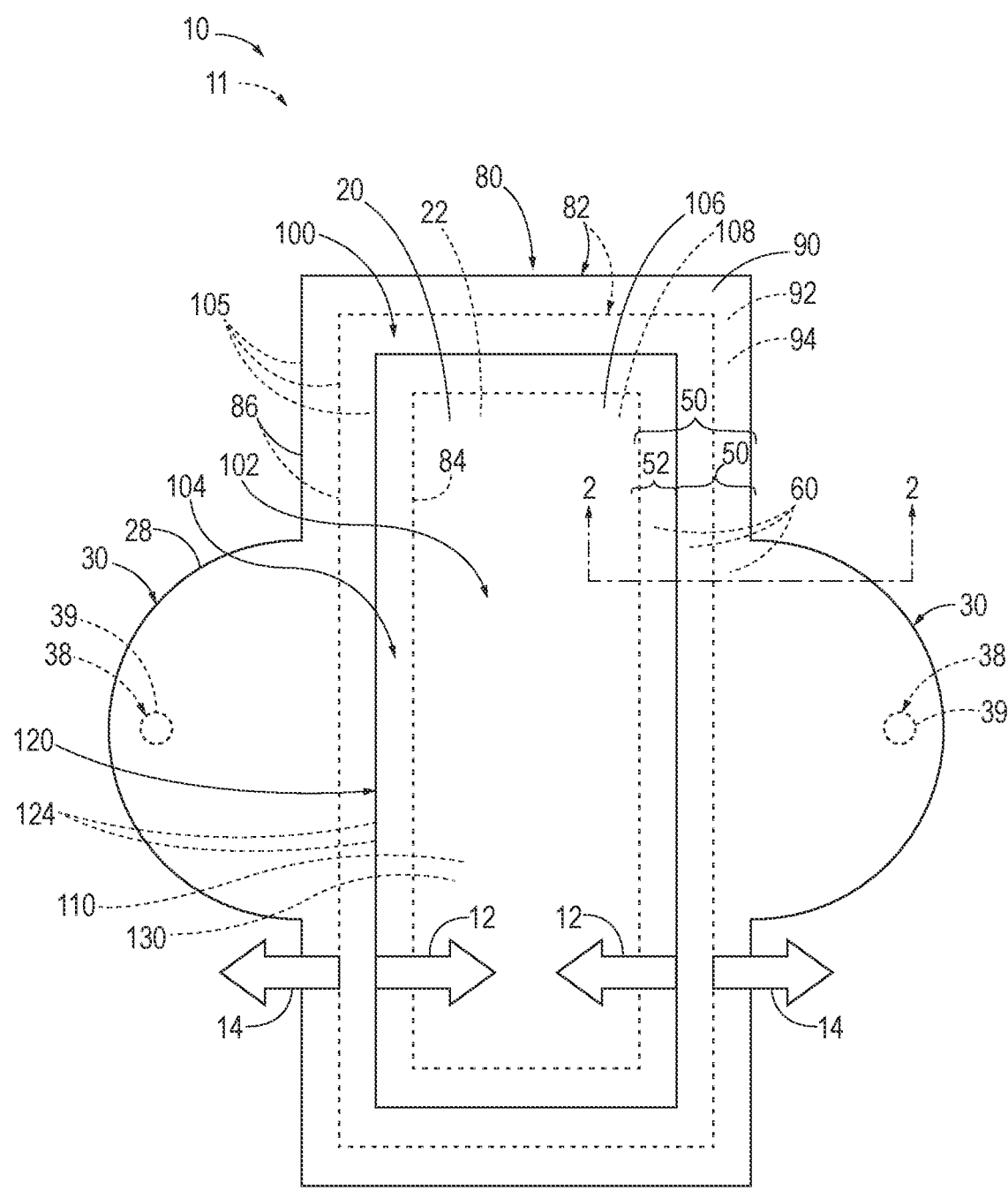
FIG. 1 is a schematic top plan view illustrating examples of reusable absorbent accessories with moisture capture assemblies according to the present disclosure.

FIGS. 1-7 provide examples of reusable absorbent accessories 10 including moisture capture assemblies 100 and/or of methods 200 of manufacturing reusable absorbent accessories 10, according to the present disclosure. Elements that serve a similar, or at least substantially similar, purpose are labeled with like numbers in each of FIGS. 1-7, and these elements may not be discussed in detail herein with reference to each of FIGS. 1-7. Similarly, all elements may not be labeled in each of FIGS. 1-7, but reference numerals associated therewith may be utilized herein for consistency. Elements, components, and/or features that are discussed herein with reference to one or more of FIGS. 1-7 may be included in and/or utilized with any of FIGS. 1-7 without departing from the scope of the present disclosure. In general, elements that are likely to be included in a particular embodiment or example are illustrated in solid lines, while elements that are optional are illustrated in dashed lines. However, elements that are shown in solid lines may not be essential and, in some embodiments or examples, may be omitted without departing from the scope of the present disclosure.

Figure 2:
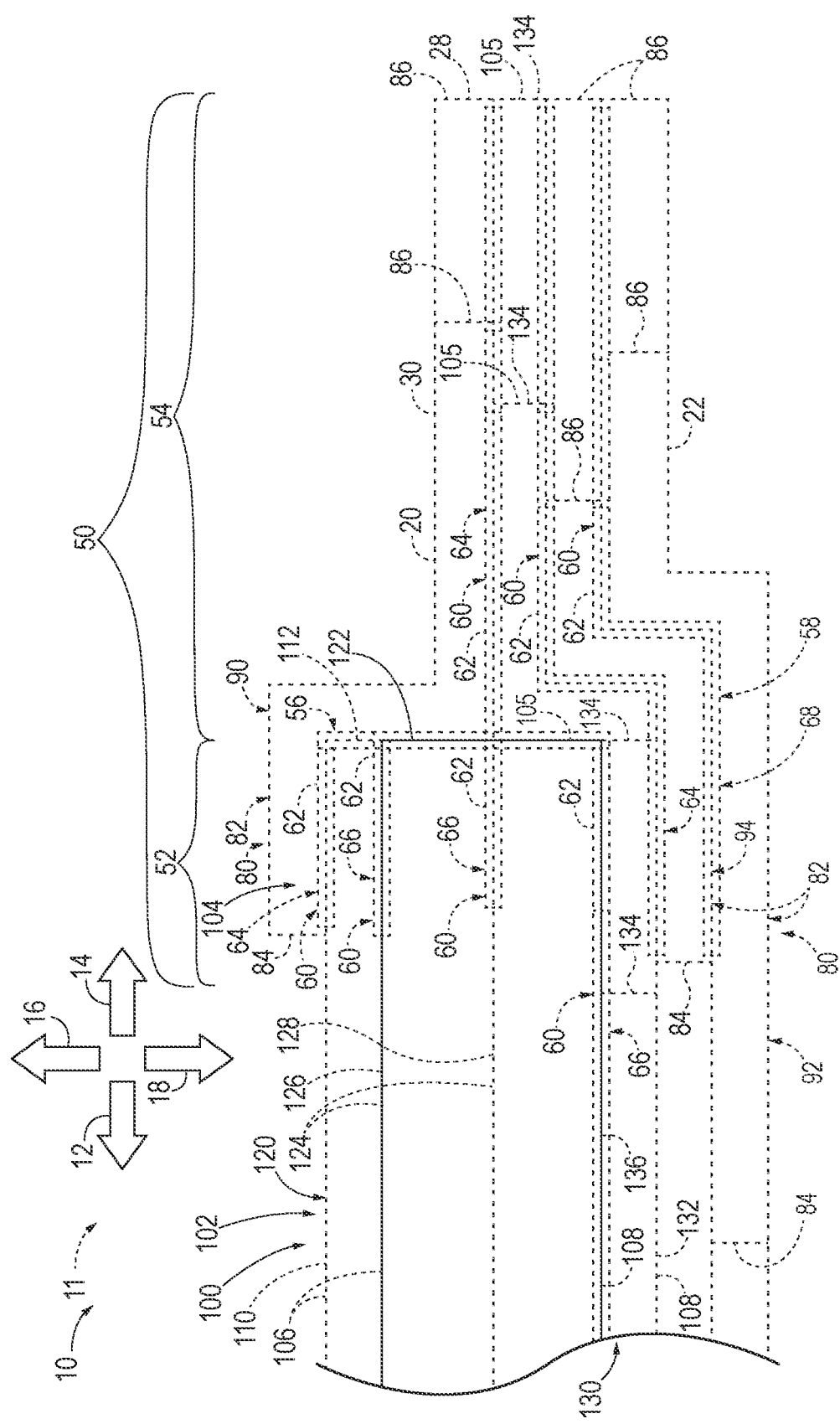
FIG. 2 is a schematic fragmentary cross-sectional side elevation view taken along the line 2-2 of FIG. 1 illustrating examples of reusable absorbent accessories with moisture capture assemblies according to the present disclosure.
Figure 3:
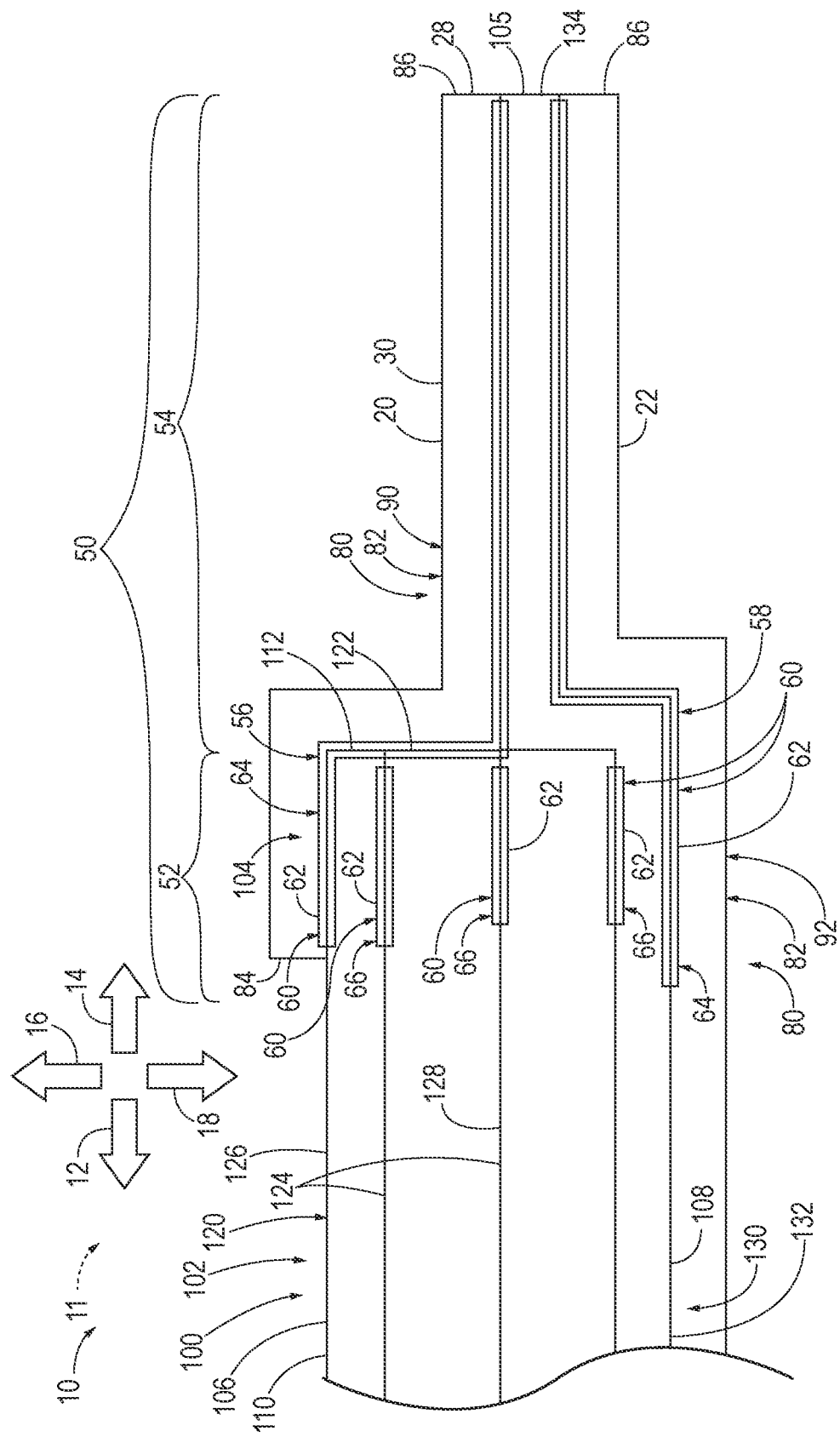
FIG. 3 is a schematic fragmentary cross-sectional side elevation view taken along the line 2-2 of FIG. 1 illustrating an example of a reusable absorbent accessory with a moisture capture assembly according to the present disclosure.
Figure 4:
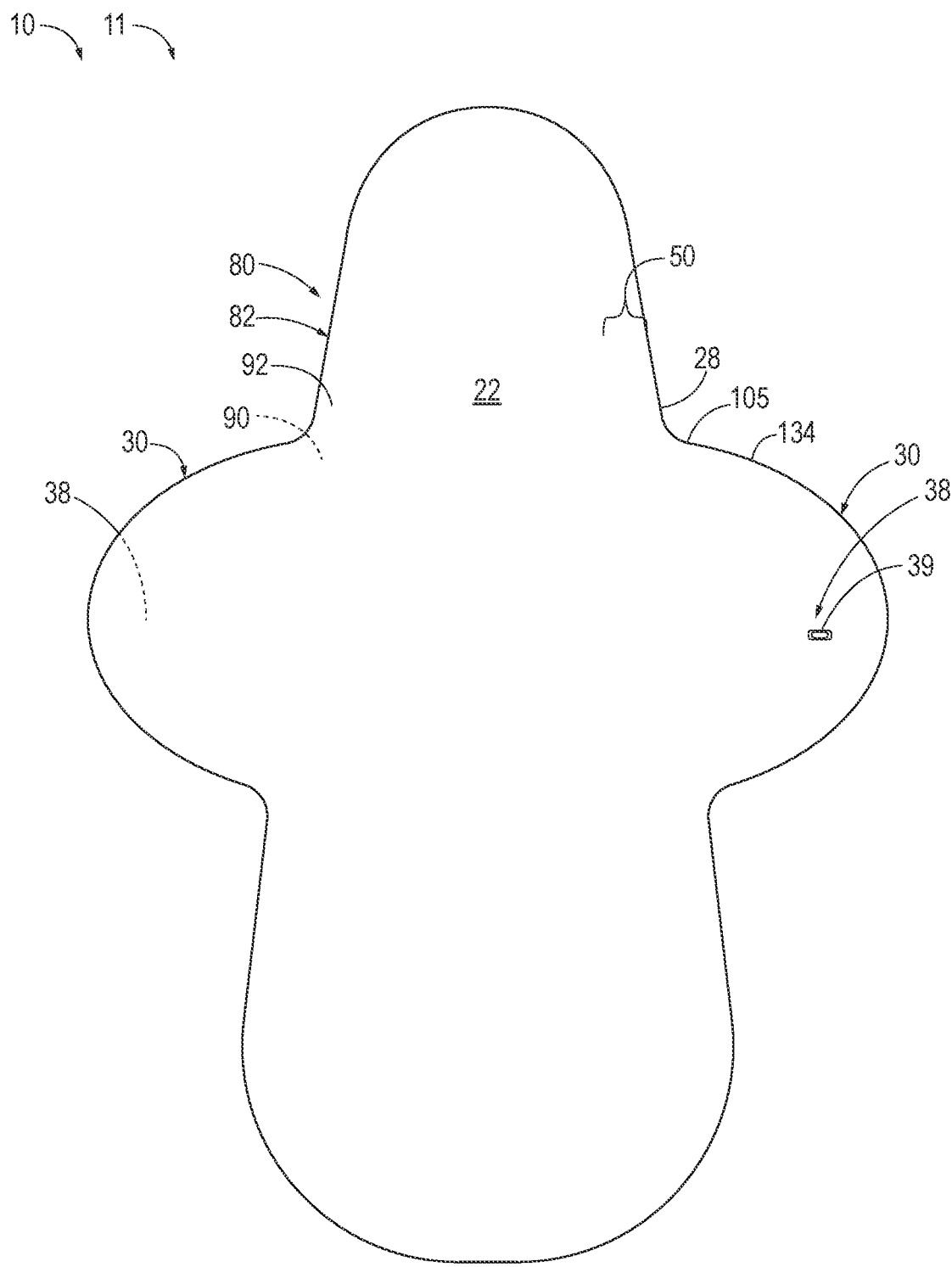
FIG. 4 is a plan view illustrating an exterior of an example reusable absorbent accessory according to the present disclosure.
Figure 5:
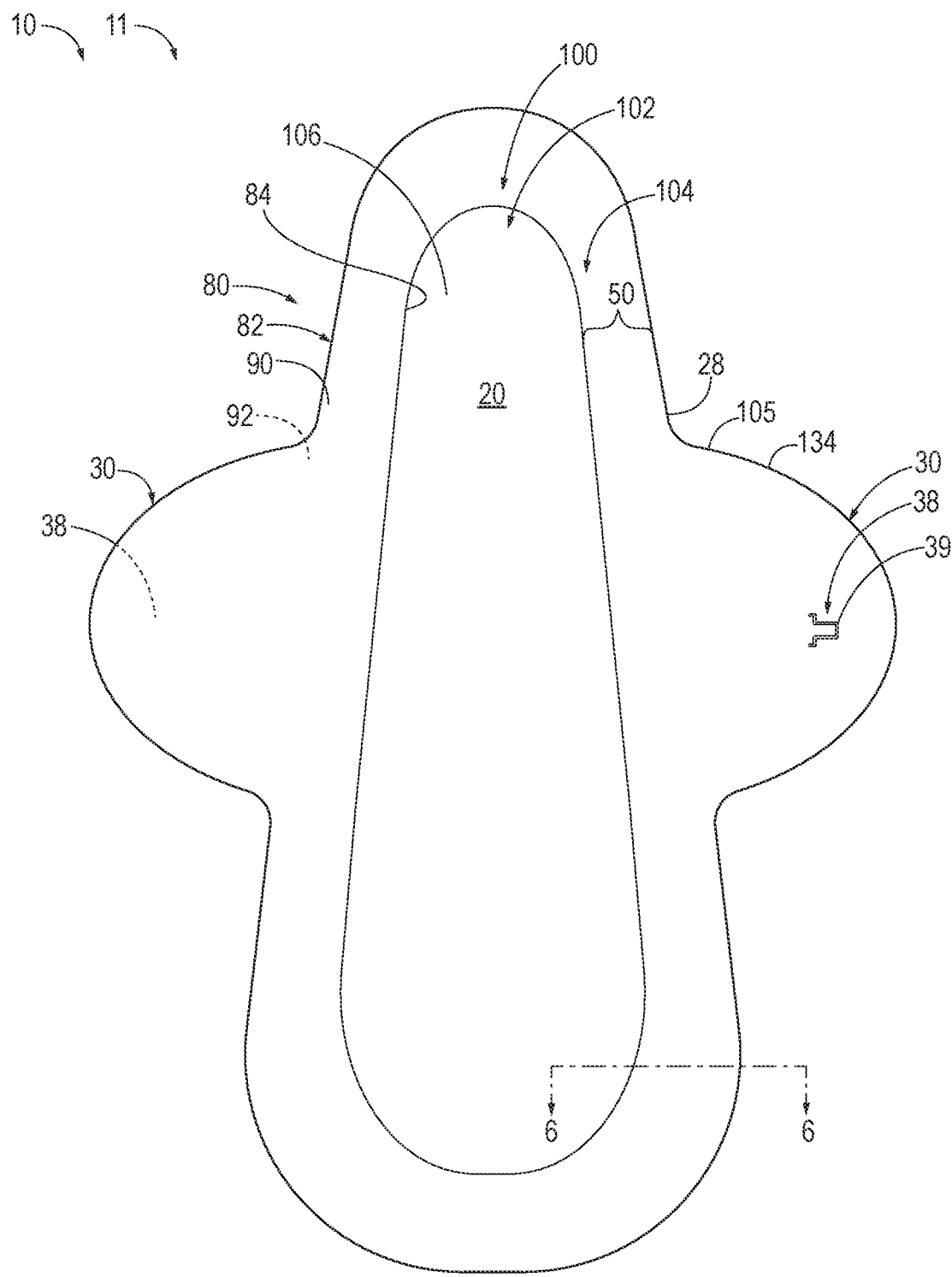
FIG. 5 is a plan view illustrating an interior of the example reusable absorbent accessory of FIG. 4.
Figure 6:
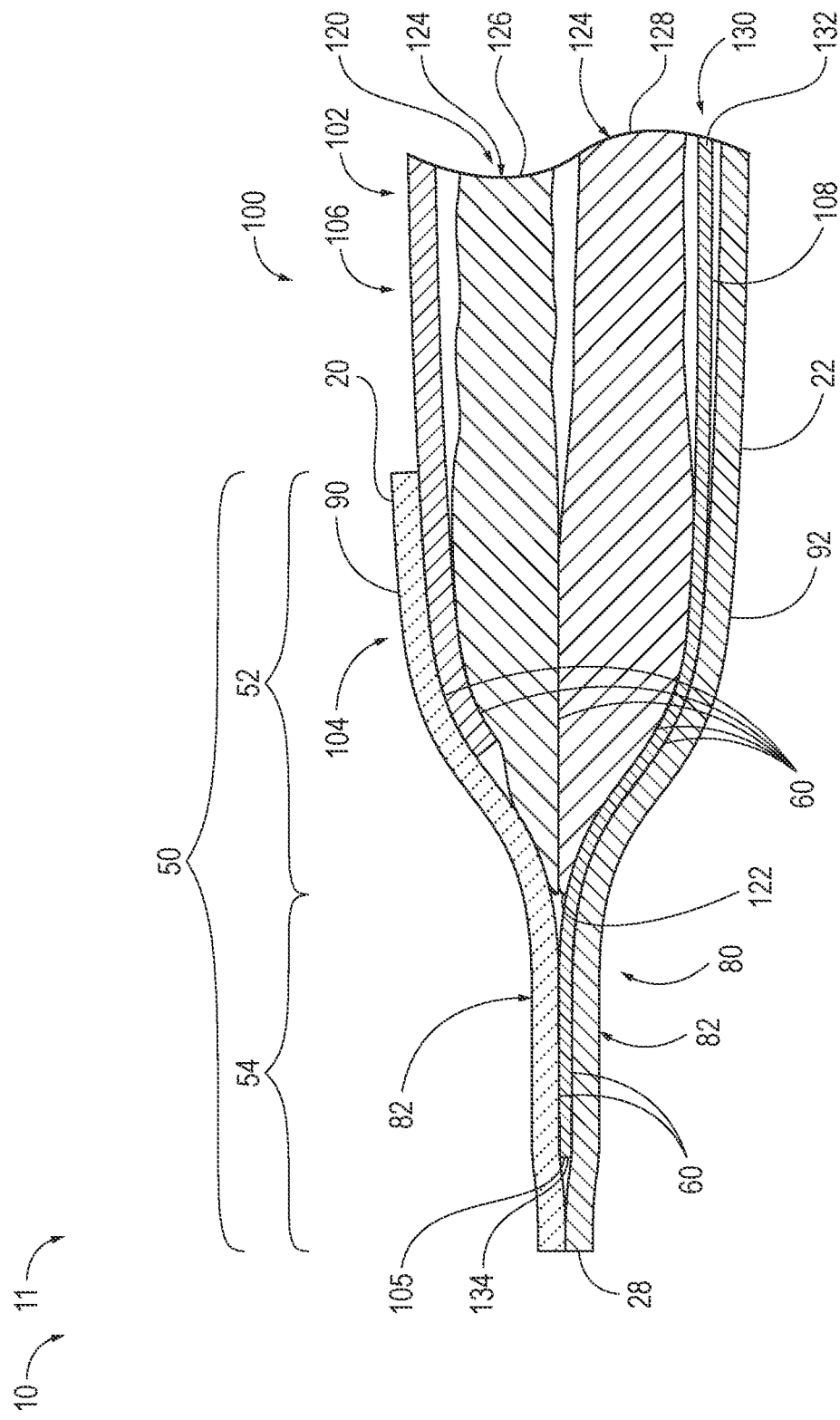
FIG. 6 is a fragmentary cross-sectional side elevation view of the example reusable absorbent accessory of FIG. 4 taken along the line 6-6 of FIG. 5.

FIG. 1 is a schematic top plan view illustrating examples of reusable absorbent accessories 10 according to the present disclosure, while FIGS. 2-3 are schematic cross-sectional side views of reusable absorbent accessories 10 as viewed along the line 2-2 in FIG. 1. FIGS. 4-6 illustrate portions of an example reusable absorbent accessory 11, which is an example of reusable absorbent accessory 10. In particular, the schematic cross-sectional side view of FIG. 3 corresponds to the construction of example reusable absorbent accessory 11, as described in more detail herein.

As schematically illustrated in FIGS. 1-3 and less schematically illustrated in FIGS. 4-6, a reusable absorbent accessory 10 is configured to be worn by a wearer includes a bonded region 50, a reusable absorbent accessory base 80, and a moisture capture assembly 100 bonded to reusable absorbent accessory base 80 within bonded region 50. In particular, and as described in more detail herein, moisture capture assembly 100 is bonded to reusable absorbent accessory base 80 with a plurality of adhesive bonds 60 that are formed within bonded region 50. In some examples, bonded region 50 may be described as defining a closed region and/or may be described as being a ring or hoop, although bonded region 50 is not limited to being circular and in most instances will not be circular. That is, bonded region 50 is continuous around a perimeter region of moisture capture assembly 100.

As schematically illustrated in FIGS. 1-3, moisture capture assembly 100 includes an assembly interior side 106 that faces the wearer when reusable absorbent accessory 10 is worn by the wearer and an assembly exterior side 108 that faces away from the wearer when the reusable absorbent accessory 10 is worn by the wearer. As additionally schematically illustrated in FIGS. 1-3, moisture capture assembly 100 further includes a moisture retention portion 120 that is configured to absorb and retain moisture from the user, as well as an anti-leak portion 130 that is configured to restrict moisture from exiting moisture retention portion 120. In the present disclosure, moisture retention portion 120 also may be referred to as a moisture retention subassembly 120, and anti-leak portion 130 may be referred to as an anti-leak subassembly 130.

Reusable absorbent accessory 10 may be configured to absorb and retain any of a variety of fluids, such as may be associated with and/or produced by the wearer while the wearer wears the reusable absorbent accessory. For example, reusable absorbent accessory 10 may be configured to absorb and retain blood and/or other menstrual fluids produced by the wearer, and/or to absorb and retain urine produced by the wearer, such as may be associated with an incontinence condition. However, unlike traditional reusable absorbent accessories that include absorbent features that are bulky and/or that are assembled within the reusable absorbent accessory with bulky stitching, the bonded construction of reusable absorbent accessory 10 as disclosed herein allows for reusable absorbent accessory 10 to be low-profile and discreet without compromising the leak-proof properties of the reusable absorbent accessory. Reusable absorbent accessory 10 may include and/or be any of a variety of reusable absorbent accessories and/or worn accessories, such as a menstrual pad and/or an incontinence pad. Additionally or alternatively, in some examples, reusable absorbent accessory 10 is configured to be worn in conjunction with a separate garment, such as a panty.

In various examples according to the present disclosure, reusable absorbent accessory 10 is configured to be washed and re-worn numerous times. In this manner, in such examples, reusable absorbent accessory 10 is distinct from a disposable absorbent accessory that is configured to be worn only once, or only a small number of times, before being disposed and replaced.

As schematically illustrated in FIGS. 2-3, the plurality of adhesive bonds 60 includes an internal peripheral bond 56 that is positioned on an interior side of at least a portion of moisture capture assembly 100 and an external peripheral bond 58 positioned on an exterior side of at least a portion of the moisture capture assembly. Specifically, each of internal peripheral bond 56 and external peripheral bond 58 extends at least substantially around a perimeter of moisture capture assembly 100. As described in more detail herein, configuring reusable absorbent accessory 10 to include each of internal peripheral bond 56 and external peripheral bond 58 may enhance the moisture retention properties of moisture capture assembly 100.

As described in more detail herein, various components and/or features of reusable absorbent accessory 10 may be described with reference to directions defined relative to the reusable absorbent accessory. For example, and as schematically illustrated in FIGS. 1-3, reusable absorbent accessory 10 and/or a portion thereof may be described as defining a laterally inward direction 12 and a laterally outward direction 14, such that laterally inward direction 12 generally is directed toward a central region of reusable absorbent accessory 10, and such that laterally outward direction 14 is opposite the laterally inward direction. Additionally, and as schematically illustrated in FIGS. 2-3, reusable absorbent accessory 10 may be described as defining a transversely inward direction 16 that is directed toward the wearer when reusable absorbent accessory 10 is worn by the wearer and a transversely outward direction 18 that is opposite the transversely inward direction. In this manner, each of transversely inward direction 16 and transversely outward direction 18 is perpendicular to each of laterally inward direction 12 and laterally outward direction 14. As a more specific example, and as schematically illustrated in FIGS. 2-3, assembly interior side 106 of moisture capture assembly 100 may be described as being spaced apart from assembly exterior side 108 of the moisture capture assembly along transversely inward direction 16. As used herein, a first component may be described as being positioned on an interior side of a second component when the first component is at least partially offset from the second component along transversely inward direction 16. Similarly, as used herein, a first component may be described as being positioned on an exterior side of a second component when the first component is at least partially offset from the second component along transversely outward direction 18.

Although FIGS. 1-3 schematically illustrate reusable absorbent accessory 10 as being generally flat and/or planar, this is not required of reusable absorbent accessory 10 in all examples and/or configurations. Accordingly, it is within the scope of the present disclosure that each of laterally inward direction 12, laterally outward direction 14, transversely inward direction 16, and/or transversely outward direction 18 is not oriented in the same absolute direction at all locations on reusable absorbent accessory 10. Stated differently, laterally inward direction 12, laterally outward direction 14, transversely inward direction 16, and transversely outward direction 18 may be described as representing directions that are relative to a particular location and/or region of reusable absorbent accessory 10, irrespective of the configuration and/or orientation of the reusable absorbent accessory away from such a particular location and/or region.

Each of the plurality of adhesive bonds 60 may operate to bond any of a variety of portions and/or components of reusable absorbent accessory 10 to one another. In particular, and as schematically illustrated in FIGS. 2-3, the plurality of adhesive bonds 60 may include one or more capture assembly-base bonds 64, each of which operates to bond at least a portion of moisture capture assembly 100 to at least a portion of reusable absorbent accessory base 80, as described in more detail herein. Additionally or alternatively, and as schematically illustrated in FIGS. 2-3, the plurality of adhesive bonds 60 may include one or more capture assembly internal bonds 66, each of which operates to bond two or more distinct portions and/or components of moisture capture assembly 100 to one another, as described in more detail herein. Additionally or alternatively, and as schematically illustrated in FIGS. 2-3, the plurality of adhesive bonds 60 may include one or more base internal bonds 68, each of which operates to bond two or more distinct portions and/or components of reusable absorbent accessory base 80 to one another, as described in more detail herein. In some examples, at least one adhesive bond 60 may be described as representing two or more of capture assembly-base bond 64, capture assembly internal bond 66, and/or base internal bond 68. For example, in an example in which a particular adhesive bond 60 operates to bond a portion of moisture capture assembly 100 to each of reusable absorbent accessory base 80 and to another portion of the moisture capture assembly, such an adhesive bond may be described as being each of a capture assembly-base bond 64 and a capture assembly internal bond 66.

In various examples, the plurality of adhesive bonds 60 may include a plurality of capture assembly-base bonds 64, a plurality of capture assembly internal bonds 66, and/or a plurality of base internal bonds 68. Accordingly, descriptions and/or references herein to a configuration and/or feature of capture assembly-base bond 64, of capture assembly internal bond 66, and/or of base internal bond 68 are to be understood to referring to at least one such adhesive bond 60 of reusable absorbent accessory 10 without requiring that every such adhesive bond of the reusable absorbent accessory exhibits such a configuration and/or feature.

Each adhesive bond 60 may be formed in any of a variety of manners. For example, and as schematically illustrated in FIGS. 2-3, each adhesive bond 60 may be formed by an adhesive material 62 that is applied to reusable absorbent accessory base 80 and/or to moisture capture assembly 100 to assemble reusable absorbent accessory 10. In such examples, adhesive material 62 may include and/or be any of a variety of materials, examples of which include a tape, an elastic tape, a film, an elastic film, an adhesive, a spray-on adhesive, a liquid curable adhesive, and/or a thermoset adhesive. Additionally or alternatively, one or more adhesive bonds 60 may be formed at least partially via a thermocompression process, such as by applying heat and/or pressure to adhesive material 62 during the manufacture of reusable absorbent accessory 10.

In some examples, adhesive bond 60 and/or adhesive material 62 is water-resistant, water-repellent, and/or waterproof. Accordingly, in such examples, and as discussed in more detail herein, each such adhesive bond 60 may form a barrier to the passage of moisture and/or bodily fluids, such as to retain such moisture and/or bodily fluids within moisture capture assembly 100 and/or to restrict moisture from entering the moisture capture assembly from an external environment.

In the schematic cross-sectional side views of FIGS. 2-3, each adhesive bond 60 is indicated by an elongate rectangle that overlaps two or more structures and/or layers of reusable absorbent accessory base 80 and/or of moisture capture assembly 100. In particular, although FIGS. 2-3 schematically illustrate each adhesive bond 60 as having an extent along transversely inward direction 16 and/or along transversely outward direction 18, such an illustration is presented for clarity only, and it is to be understood that each adhesive bond 60 and/or the associated adhesive material 62 may exist primarily, solely, and/or at least substantially between, or at an interface between, the structures that are bonded together via the adhesive bond. Additionally or alternatively, the associated adhesive material may extend into (e.g., having wicked into) the structures that are bonded together via the adhesive bond. Similarly, it is to be understood that the schematic representations of FIGS. 2-3 represent the illustrated components as having a greatly exaggerated extent along the direction parallel to transversely inward direction 16 and transversely outward direction 18 for purposes of clarity.

In the present disclosure, description of locations and/or configurations of various adhesive bonds 60 and/or of various layers of reusable absorbent accessory 10 often are presented with reference to the cross-sectional views of FIGS. 2-3 and 6. Although the cross-sectional views of FIGS. 2-3 are taken along the line 2-2 of FIG. 1, it is to be understood that such cross-sectional views (including the cross-sectional views of FIG. 6) may correspond to any suitable portion of reusable absorbent accessory 10 and/or of bonded region 50. In this manner, the cross-sectional views of FIGS. 2-3 and 6 may be understood as being representative of any and/or every location along a perimeter of moisture capture assembly 100. In particular, in some examples, the constructions illustrated in the cross-sectional views of FIGS. 2-3 and 6 extend fully (or at least substantially fully) around a perimeter of moisture capture assembly 100. However, this is not required of all examples of reusable absorbent accessory 10, and it additionally is within the scope of the present disclosure that the construction of reusable absorbent accessory 10 may vary at distinct locations along a perimeter of moisture capture assembly 100.

Reusable absorbent accessory 10 may include any of a variety of features for accommodating and/or engaging the wearer's body. As schematically illustrated in FIGS. 1-3, reusable absorbent accessory 10 may be described as including a reusable absorbent accessory interior surface 20 that faces the wearer when the reusable absorbent accessory is worn by the wearer as well as a reusable absorbent accessory exterior surface 22 that faces away from the wearer when the reusable absorbent accessory is worn by the wearer. In particular, in some examples, at least a portion of reusable absorbent accessory interior surface 20 is configured to directly contact the wearer when reusable absorbent accessory 10 is worn by the wearer. Stated differently, in some examples, reusable absorbent accessory 10 is configured such that, when the reusable absorbent accessory is worn by the wearer, no portion of the reusable absorbent accessory is positioned directly between reusable absorbent accessory interior surface 20 and the wearer. Similarly, in some examples, reusable absorbent accessory 10 is configured such that, when the reusable absorbent accessory is worn by the wearer, no portion of the reusable absorbent accessory is positioned distal the wearer relative to reusable absorbent accessory exterior surface 22.

In some examples, and as discussed, reusable absorbent accessory 10 is configured to be utilized and/or worn in conjunction with a separate garment, such as an undergarment and/or a panty. In such examples, reusable absorbent accessory exterior surface 22 may be configured to face and/or engage the separate garment while reusable absorbent accessory 10 is worn by the wearer. As a more specific example, reusable absorbent accessory 10 may be a menstrual pad and/or an incontinence pad that is configured to be positioned between an undergarment (e.g., a panty) and the wearer's crotch region. Additionally or alternatively, in some examples, and as schematically illustrated in FIGS. 1-3 and less schematically illustrated in FIGS. 4-5, reusable absorbent accessory 10 includes one or more wing extensions 30 configured to engage a separate garment (e.g., a panty) and/or to operatively secure the reusable absorbent accessory relative to the separate garment. In particular, in some such examples, wing extension(s) 30 are configured to at least partially wrap around the separate garment to secure reusable absorbent accessory 10 relative to the separate garment. In some examples, and as schematically illustrated in FIG. 1, each wing extension 30 includes a reusable absorbent accessory attachment feature 38 configured to secure reusable absorbent accessory 10 relative to the separate garment. In particular, in some such examples, reusable absorbent accessory 10 includes a pair of wing extensions 30, each of which includes reusable absorbent accessory attachment feature 38 that includes and/or is a reusable absorbent accessory attachment fastener 39 for selectively coupling the pair of wing extensions to one another. In such examples, each absorbent accessory attachment fastener 39 may include and/or be any of a variety of mechanical fasteners, examples of which include a hook, a hook receiver, a hook-and-loop fastener, etc.

As schematically illustrated in FIGS. 1-3, moisture capture assembly 100 may be described as including a moisture capture assembly central region 102 and a moisture capture assembly peripheral region 104 that circumferentially encloses the moisture capture assembly central region. Accordingly, and as schematically illustrated in FIGS. 1-3, bonded region 50 may be described as including at least a portion of moisture capture assembly peripheral region 104. Additionally or alternatively, bonded region 50 may be described as extending at least substantially around and/or along a perimeter of moisture capture assembly peripheral region 104.

As additionally schematically illustrated in FIGS. 1-3, reusable absorbent accessory base 80 may be described as defining a reusable absorbent accessory lateral edge 28, such that at least a portion of the moisture capture assembly is spaced apart from the reusable absorbent accessory lateral edge along laterally inward direction 12. That is, reusable absorbent accessory lateral edge 28 may refer to a terminal edge of reusable absorbent accessory base 80, and/or of any other component of reusable absorbent accessory 10 that extends fully to a terminal edge of the reusable absorbent accessory. In some examples, and as schematically illustrated in FIGS. 1-3, each wing extension 30 defines at least a portion of reusable absorbent accessory lateral edge 28.

In some examples, and as schematically illustrated in FIGS. 1-3, bonded region 50 extends from moisture capture assembly peripheral region 104 toward, and/or fully to, reusable absorbent accessory lateral edge 28. Similarly, in some examples, and as schematically illustrated in FIGS. 1-3, a portion of moisture capture assembly 100 extends fully to reusable absorbent accessory lateral edge 28. As a more specific example, moisture capture assembly 100 may be described as including and terminating at a moisture capture assembly lateral edge 105, which may define reusable absorbent accessory lateral edge 28. However, this is not required, and it additionally is within the scope of the present disclosure that moisture capture assembly 100 does not extend to reusable absorbent accessory lateral edge 28, such that moisture capture assembly lateral edge 105 is spaced apart from reusable absorbent accessory lateral edge 28 along laterally inward direction 12.

Bonded region 50 additionally or alternatively may be characterized with reference to a lateral edge of a portion of moisture capture assembly 100. In particular, and as schematically illustrated in FIGS. 1-3, moisture retention portion 120 of moisture capture assembly 100 may be described as including and terminating at a moisture retention portion lateral edge 122. As additionally schematically illustrated in FIGS. 1-3, bonded region 50 may be described as including a laterally inward portion 52 that extends from moisture retention portion lateral edge 122 toward moisture capture assembly central region 102 along laterally inward direction 12 and a laterally outward portion 54 that extends from moisture retention portion lateral edge 122 away from moisture retention portion 120 along laterally outward direction 14. In particular, in some examples, bonded region 50 consists of laterally inward portion 52 and laterally outward portion 54, which are non-overlapping and immediately adjacent to one another. In some examples, and as schematically illustrated in FIGS. 2-3 and less schematically illustrated in FIG. 6, moisture capture assembly lateral edge 105 is spaced apart from moisture retention portion lateral edge 122 along laterally outward direction 14. However, this is not required of all examples of moisture capture assembly, and it additionally is within the scope of the present disclosure that moisture retention portion lateral edge 122 is aligned with and/or defines moisture capture assembly lateral edge 105.

Reusable absorbent accessory base 80 may have any of a variety of constructions. In various examples, and as schematically illustrated in FIGS. 1-3 and less schematically illustrated in FIGS. 4-6, reusable absorbent accessory base 80 includes one or more base layers 82. In particular, in some examples, at least one base layer 82 is bonded to at least a portion of moisture capture assembly 100 via a corresponding capture assembly-base bond 64.

In various examples, and as schematically illustrated in FIGS. 1-3, base layer(s) 82 include an interior base layer 90 that forms at least a portion of reusable absorbent accessory interior surface 20 and/or an exterior base layer 92 that forms at least a portion of reusable absorbent accessory exterior surface 22. As schematically illustrated in FIG. 2, base layer(s) 82 further may include an intermediate base layer 94 that is positioned at least partially between one other base layer 82 and moisture capture assembly 100, and/or between two other base layers. In some examples, intermediate base layer 94 also may define at least a portion of reusable absorbent accessory interior surface 20 and/or of reusable absorbent accessory exterior surface 22; however, for the purposes of the present disclosure, such a base layer still is termed an intermediate base layer on account of being positioned between interior base layer 90 and exterior base layer 92. In this manner, intermediate base layer 94 may refer to any base layer 82 that overlies at least a portion of exterior base layer 92 and that underlies at least a portion of interior base layer 90. Each base layer 82 (e.g., interior base layer 90, exterior base layer 92, and/or intermediate base layer 94) may be formed of any of a variety of materials. As examples, each base layer 82 may be at least partially formed of a natural fiber, cotton, a synthetic fiber, polyester, nylon, Spandex™ fabric, and/or combinations thereof.

In the present disclosure, each base layer 82 may be at least partially characterized with reference to one or more lateral edges thereof. For example, and as schematically illustrated in FIGS. 2-3, each base layer 82 may be described as including and terminating at a respective base layer lateral inward edge 84, such that the base layer extends away from the respective base layer lateral inward edge along laterally outward direction 14. Additionally or alternatively, and as schematically illustrated in FIGS. 2-3, each base layer 82 may be described as including and terminating at a respective base layer lateral outward edge 86, such that the base layer extends away from the respective base layer lateral outward edge along laterally inward direction 12.

As used herein, directional terms such as "overlie," "above," "underlie," "below," and the like generally refer to relative positions as viewed from the side of reusable absorbent accessory 10 with reusable absorbent accessory interior surface 20 facing upwards, as in the schematic views of FIGS. 2-3. In particular, a first component may be described as overlying a second component, and/or as being positioned above the second component, when the first component is spatially offset from the second component along transversely inward direction 16. Similarly, a first component may be described as underlying a second component, and/or as being positioned under the second component, when the first component is spatially offset from the second component along transversely outward direction 18.

Moisture capture assembly 100 and/or moisture retention portion 120 may have any of a variety of constructions for absorbing and capturing moisture from the wearer. In some examples, and as schematically illustrated in FIGS. 2-3 and less schematically illustrated in FIG. 6, moisture retention portion 120 includes one or more moisture retention layers 124, such as a first moisture retention layer 126 and a second moisture retention layer 128. In some such examples, and as schematically illustrated in FIGS. 2-3 and less schematically illustrated in FIG. 6, each of first moisture retention layer 126 and second moisture retention layer 128 extends to (and thus at least partially defines) moisture retention portion lateral edge 122. When present, first moisture retention layer 126 and second moisture retention layer 128 may be formed of the same and/or similar materials, or may be at least partially formed of different materials.

In some examples, first moisture retention layer 126 and second moisture retention layer 128 are operatively coupled to one another. In particular, and as schematically illustrated in FIGS. 2-3, first moisture retention layer 126 and second moisture retention layer 128 may be bonded to one another via at least one capture assembly internal bond 66. In such examples, and as schematically illustrated in FIGS. 2-3 and less schematically illustrated in FIG. 6, capture assembly internal bond 66 that bonds first moisture retention layer 126 and second moisture retention layer 128 to one another may be positioned only (e.g., fully and/or exclusively) or at least substantially in laterally inward portion 52 of bonded region 50. However, this is not required of all examples of moisture capture assembly 100, and it also is within the scope of the present disclosure that capture assembly internal bond 66 that bonds first moisture retention layer 126 and second moisture retention layer 128 may be positioned within each of laterally inward portion 52 and laterally outward portion 54 of bonded region 50.

In some examples, and as schematically illustrated in FIGS. 1-3 and less schematically illustrated in FIGS. 5-6, moisture retention portion 120 of moisture capture assembly 100 includes a wicking layer 110 that is configured to wick moisture away from the wearer. In particular, in such examples, wicking layer 110 may be configured to draw moisture away from the wearer, such as via capillary action, and to direct and/or convey the moisture to moisture retention layer(s) 124. In such examples, wicking layer 110 may be positioned and/or bonded within moisture capture assembly 100 in any of a variety of manners. For example, and as schematically illustrated in FIGS. 1-3 and less schematically illustrated in FIGS. 5-6, wicking layer 110 may extend within each of moisture capture assembly central region 102 and moisture capture assembly peripheral region 104. In some examples, wicking layer 110 is operatively coupled to moisture retention portion 120, such as to first moisture retention layer 126. In particular, in some examples, and as schematically illustrated in FIGS. 2-3, wicking layer 110 and moisture retention portion 120 are bonded to one another via at least one adhesive bond 60, such as via at least one capture assembly internal bond 66. In some examples, and as schematically illustrated in FIGS. 2-3 and less schematically illustrated in FIGS. 5-6, wicking layer 110 at least partially defines assembly interior side 106 of moisture capture assembly 100.

With particular reference to the cross-sectional views of FIGS. 2-3 and 6, a configuration of wicking layer 110 also may be characterized with reference to a wicking layer lateral edge 112 thereof, which represents a terminal edge of the wicking layer. For example, and as schematically illustrated in FIGS. 2-3 and less schematically illustrated in FIG. 6, wicking layer lateral edge 112 may be aligned with moisture retention portion lateral edge 122. However, this is not required of all examples of moisture capture assembly 100, and it additionally is within the scope of the present disclosure that wicking layer lateral edge 112 may be spaced apart from moisture retention portion lateral edge 122 along laterally inward direction 12 or along laterally outward direction 14. In particular, in an example in which wicking layer lateral edge 112 is spaced apart from moisture retention portion lateral edge 122 along laterally outward direction 14, wicking layer 110 may extend within each of laterally inward portion 52 and laterally outward portion 54 of bonded region 50. In some examples, such as when wicking layer lateral edge 112 is aligned with moisture retention portion lateral edge 122 or is spaced apart from the moisture retention portion lateral edge along laterally outward direction 14, the wicking layer lateral edge may define moisture capture assembly lateral edge 105. Alternatively, in some examples, such as when wicking layer lateral edge 112 is spaced apart from moisture retention portion lateral edge 122 along laterally inward direction 12, the wicking layer lateral edge also may be spaced apart from moisture capture assembly lateral edge 105 along the laterally inward direction.

As used herein, the term "aligned," as used to describe a relative position of a first edge relative to a second edge, generally refers to a configuration in which the first edge and the second edge are positioned at respective locations that are not spatially separated from one another along laterally inward direction 12 or along laterally outward direction 14, but which may be spatially separated from one another along transversely inward direction 16 or along transversely outward direction 18. However, it is to be understood that a description herein of two or more components as being "aligned" does not necessarily mean that the two or more components are exactly and/or precisely aligned with one another. For example, as known in the art, garment construction is not perfect, and the imprecision introduced by human- and/or machine-performed manufacturing can introduce slight misalignments between components that nominally are intended or designed to be aligned with one another. Accordingly, for the purposes of the present disclosure, the term "aligned" is intended to encompass configurations in which the components are perfectly aligned, as well as configurations in which the components are slightly misaligned as a result of manufacturing tolerances.

Anti-leak portion 130 of moisture capture assembly 100 may include any of a variety of components and/or features for restricting moisture from exiting the moisture capture assembly. For example, and as schematically illustrated in FIGS. 2-3 and less schematically illustrated in FIG. 6, anti-leak portion 130 may include and/or be a moisture barrier layer 132 that is operatively coupled to moisture retention portion 120. In particular, in some examples, and as schematically illustrated in FIGS. 2-3, moisture barrier layer 132 is bonded to moisture retention portion 120 via at least one adhesive bond 60, such as via at least one capture assembly internal bond 66. When present, moisture barrier layer 132 may include and/or be any of a variety of materials, such as a moisture-impermeable film. Additionally or alternatively, in some examples, and as schematically illustrated in FIG. 2, anti-leak portion 130 may include and/or be a moisture barrier treatment 136 and/or a moisture barrier film that is applied to moisture retention portion 120, such as to moisture retention layer 124 (e.g., to second moisture retention layer 128). In some examples, and as schematically illustrated in FIGS. 2-3 and less schematically illustrated in FIG. 6, moisture barrier layer 132 at least partially defines assembly exterior side 108 of moisture capture assembly 100.

Each portion of moisture capture assembly 100 may be formed of any of a variety of materials. As examples, each of moisture capture assembly 100, moisture retention portion 120, first moisture retention layer 126, second moisture retention layer 128, wicking layer 110, and/or moisture barrier layer 132 may be at least partially formed of a natural fiber, cotton, a synthetic fiber, polyester, nylon, Spandex™ fabric, and/or combinations thereof.

With particular reference to the cross-sectional views of FIGS. 2-3 and 6, a configuration of moisture barrier layer 132 also may be characterized with reference to a moisture barrier layer lateral edge 134 thereof, which represents a terminal edge of the moisture barrier layer. For example, and as schematically illustrated in FIGS. 2-3 and less schematically illustrated in FIG. 6, moisture barrier layer lateral edge 134 may be spaced apart from moisture retention portion lateral edge 122 along laterally outward direction 14. In particular, in such examples, moisture barrier layer 132 may extend within each of laterally inward portion 52 and laterally outward portion 54 of bonded region 50. However, this is not required of all examples of moisture capture assembly 100, and it additionally is within the scope of the present disclosure that moisture barrier layer lateral edge 134 may be aligned with moisture retention portion lateral edge 122, or may be spaced apart from the moisture retention portion lateral edge along the laterally inward direction. In some examples, such as when moisture barrier layer lateral edge 134 is aligned with moisture retention portion lateral edge 122 or is spaced apart from the moisture retention portion lateral edge along laterally outward direction 14, the moisture barrier layer lateral edge may define moisture capture assembly lateral edge 105. Alternatively, in some examples, such as when moisture barrier layer lateral edge 134 is spaced apart from moisture retention portion lateral edge 122 along laterally inward direction 12, the moisture barrier layer lateral edge also may be spaced apart from moisture capture assembly lateral edge 105 along laterally inward direction 12.

Each capture assembly-base bond 64 may have any of a variety of configurations and/or locations within reusable absorbent accessory 10 so as to bond at least a portion of moisture capture assembly 100 to at least a portion of reusable absorbent accessory base 80. In some examples, and as schematically illustrated in FIG. 2, capture assembly-base bond 64 (e.g., at least one capture assembly-base bond) is positioned only in laterally inward portion 52 of bonded region 50. Additionally or alternatively, in some examples, and as schematically illustrated in FIGS. 2-3, capture assembly-base bond 64 (e.g., at least one capture assembly-base bond) is positioned in laterally outward portion 54 of bonded region 50. Additionally or alternatively, in some examples, and as schematically illustrated in FIGS. 2-3, capture assembly-base bond 64 (e.g., at least one capture assembly-base bond) extends within each of laterally inward portion 52 and laterally outward portion 54 of bonded region 50.

Additionally, each capture assembly-base bond 64 may operate to bond any of a variety of portions of moisture capture assembly 100 to any of a variety of portions of reusable absorbent accessory base 80. In particular, in some examples, and as schematically illustrated in FIGS. 2-3, capture assembly-base bond 64 (e.g., at least one capture assembly-base bond) directly bonds at least one base layer 82 to assembly interior side 106 of moisture capture assembly 100. For example, capture assembly-base bond may operate to bond a base layer (e.g., interior base layer 90) directly to assembly interior side 106 of the moisture capture assembly (e.g., to wicking layer 110 and/or to first moisture retention layer 126).

Additionally or alternatively, in some examples, and as schematically illustrated in FIGS. 2-3, capture assembly-base bond 64 (e.g., at least one capture assembly-base bond) directly bonds at least one base layer 82 to assembly exterior side 108 of moisture capture assembly 100. For example, capture assembly-base bond 64 may operate to bond a base layer 82 (e.g., intermediate base layer 94 and/or exterior base layer 92) directly to assembly exterior side 108 of the moisture capture assembly (e.g., to second moisture retention layer 128 and/or to moisture barrier layer 132). Examples of manners in which internal peripheral bond 56, external peripheral bond 58, and anti-leak portion 130 of moisture capture assembly 100 collectively resist leakage of moisture also may be understood with reference to FIGS. 2-3. As discussed, each adhesive bond 60 may be formed by an adhesive material 62 that is water-resistant, water-repellent, and/or waterproof. Accordingly, each of internal peripheral bond 56 and external peripheral bond 58 may be understood as representing a barrier against the leakage of moisture across the bond. Similarly, moisture barrier layer 132 of anti-leak portion 130 also may be understood as representing a barrier against the leakage of moisture across the moisture barrier layer. Accordingly, and with reference to the schematic cross-sectional views of FIGS. 2-3, moisture that is incident upon moisture capture assembly 100 via assembly interior side 106 is restricted from escaping moisture retention portion 120 other than via the assembly internal side, since each other path out of the moisture retention portion is blocked by internal peripheral bond 56 and/or by moisture barrier layer 132. In this manner, anti-leak portion 130 and the plurality of adhesive bonds 60 may prevent leakage of moisture out of moisture retention portion 120 via a portion of reusable absorbent accessory base 80 underlying the moisture retention portion (e.g., via exterior base layer 92) as well as via a peripheral edge of moisture capture assembly 100. Additionally, in this manner, reusable absorbent accessory 10 also is protected against ingress of moisture from exterior the reusable absorbent accessory, since each path to moisture retention portion 120 from exterior the reusable absorbent accessory is blocked by exterior peripheral bond 58 and/or by moisture barrier layer 132. Thus, reusable absorbent accessory 10 also may protect the wearer from discomfort resulting from a wetting of moisture capture assembly 100 from moisture that did not originate from the wearer, such as water in a swimming pool occupied by the wearer, water on a seating surface upon which the wearer is seated, etc.

When present, interior base layer 90 may have any suitable position, orientation, and/or extent relative to moisture capture assembly 100, moisture retention portion 120, and/or bonded region 50. In some examples, and as schematically illustrated in FIGS. 2-3 and less schematically illustrated in FIG. 6, interior base layer 90 and moisture retention portion 120 are directly bonded to one another via a corresponding capture assembly-base bond 64 (labeled in FIGS. 2-3). In particular, in some examples, interior base layer 90 is directly bonded to wicking layer 110 and/or to moisture barrier layer 132 via respective capture assembly-base bonds 64 (labelled in FIGS. 2-3).

In some examples, and as schematically illustrated in FIGS. 2-3 and less schematically illustrated in FIG. 6, at least a portion of interior base layer 90 overlies at least a portion of moisture capture assembly 100, such as at least a portion of moisture capture assembly peripheral region 104. Stated differently, in some examples, interior base layer 90 overlies at least a portion of moisture capture assembly 100 within moisture capture assembly peripheral region 104 and/or within laterally inward portion 52 of bonded region 50. Additionally or alternatively, in some examples, and as schematically illustrated in FIGS. 2-3 and less schematically illustrated in FIG. 6, interior base layer 90 extends within each of laterally inward portion 52 and laterally outward portion 54 of bonded region 50. While FIGS. 2-3 schematically illustrate interior base layer 90 as overlying moisture capture assembly 100 as a single flat layer, this is not required of all examples of reusable absorbent accessory 10. As examples, it also is within the scope of the present disclosure that interior base layer 90 may be folded, doubled over, and/or otherwise characterized by two or more adjacent layers within a portion of moisture capture assembly peripheral region 104 within which interior base layer 90 overlies moisture capture assembly 100.

In some examples, and as schematically illustrated in FIGS. 2-3 and less schematically illustrated in FIG. 6, base layer lateral inward edge 84 of interior base layer 90 is spaced apart from moisture retention portion lateral edge 122 along laterally inward direction 12. Additionally or alternatively, in some examples, and as schematically illustrated in FIGS. 2-3, base layer lateral outward edge 86 of interior base layer 90 is aligned with moisture capture assembly lateral edge 105 and/or with moisture retention portion lateral edge 122. In other examples, and as schematically illustrated in FIG. 2, base layer lateral outward edge 86 of interior base layer 90 is spaced apart from moisture capture assembly lateral edge 105 and/or from moisture retention portion lateral edge 122 along laterally inward direction 12 or along laterally outward direction 14.

In some examples, a configuration of interior base layer 90 additionally or alternatively may be characterized with reference to wicking layer 110. For example, and as schematically illustrated in FIGS. 2-3 and less schematically illustrated in FIG. 6, base layer lateral inward edge 84 of interior base layer 90 may be spaced apart from wicking layer lateral edge 112 along laterally inward direction 12. Additionally or alternatively, in some examples, interior base layer 90 may overlie at least a portion of wicking layer 110 within moisture capture assembly peripheral region 104 and/or within laterally inward portion 52 of bonded region 50. Additionally or alternatively, in some examples, base layer lateral outward edge 86 of interior base layer 90 may be aligned with wicking layer lateral edge 112. In other examples, and as schematically illustrated in FIGS. 2-3, base layer lateral outward edge 86 of interior base layer 90 may be spaced apart from wicking layer lateral edge 112 along laterally outward direction 14.

In some examples, a configuration of interior base layer 90 additionally or alternatively may be characterized with reference to moisture barrier layer 132. For example, and as schematically illustrated in FIGS. 2-3 and less schematically illustrated in FIG. 6, base layer lateral inward edge 84 of interior base layer 90 may be spaced apart from moisture barrier layer lateral edge 134 along laterally inward direction 12. Additionally or alternatively, in some examples, interior base layer 90 may overlie at least a portion of moisture barrier layer 132 within moisture capture assembly peripheral region 104, within laterally inward portion 52 of bonded region 50, and/or within laterally outward portion 54 of the bonded region. Additionally or alternatively, in some examples, and as schematically illustrated in FIGS. 2-3 and less schematically illustrated in FIG. 6, base layer lateral outward edge 86 of interior base layer 90 may be aligned with moisture barrier layer lateral edge 134. In other examples, and as schematically illustrated in FIG. 2, base layer lateral outward edge 86 of interior base layer 90 may be spaced apart from moisture barrier layer lateral edge 134 along laterally inward direction 12 or along laterally outward direction 14.

When present, exterior base layer 92 may have any suitable position, orientation, and/or extent relative to moisture capture assembly 100, moisture retention portion 120, and/or bonded region 50. In some examples, exterior base layer 92 and moisture retention portion 120 are directly bonded to one another via a corresponding capture assembly-base bond 64. In particular, in some examples, exterior base layer 92 is directly bonded to wicking layer 110 and/or to moisture barrier layer 132 via respective capture assembly-base bonds 64.

In some examples, and as schematically illustrated in FIGS. 2-3 and less schematically illustrated in FIG. 6, at least a portion of exterior base layer 92 underlies at least a portion of moisture capture assembly 100, such as at least a portion of moisture capture assembly peripheral region 104. Stated differently, in some examples, exterior base layer 92 underlies at least a portion of moisture capture assembly 100 within moisture capture assembly peripheral region 104 and/or within laterally inward portion 52 of bonded region 50. Additionally or alternatively, in some examples, and as schematically illustrated in FIGS. 2-3 and less schematically illustrated in FIG. 6, exterior base layer 92 extends within each of laterally inward portion 52 and laterally outward portion 54 of bonded region 50. While FIGS. 2-3 schematically illustrate exterior base layer 92 as underlying moisture capture assembly 100 as a single flat layer, this is not required of all examples of reusable absorbent accessory 10. As examples, it also is within the scope of the present disclosure that exterior base layer 92 may be folded, doubled over, and/or otherwise characterized by two or more adjacent layers within a portion of moisture capture assembly peripheral region 104 within which interior base layer 90 underlies moisture capture assembly 100.

In some examples, and as schematically illustrated in FIG. 2, base layer lateral inward edge 84 of exterior base layer 92 is spaced apart from moisture retention portion lateral edge 122 along laterally inward direction 12. Additionally or alternatively, in some examples, and as schematically illustrated in FIGS. 2-3, base layer lateral outward edge 86 of exterior base layer 92 is aligned with moisture capture assembly lateral edge 105 and/or with moisture retention portion lateral edge 122. In other examples, and as schematically illustrated in FIG. 2, base layer lateral outward edge 86 of exterior base layer 92 is spaced apart from moisture capture assembly lateral edge 105 and/or from moisture retention portion lateral edge 122 along laterally inward direction 12 or along laterally outward direction 14.

In some examples, a configuration of exterior base layer 92 additionally or alternatively may be characterized with reference to wicking layer 110. For example, and as schematically illustrated in FIG. 2, base layer lateral inward edge 84 of exterior base layer 92 may be spaced apart from wicking layer lateral edge 112 along laterally inward direction 12. Additionally or alternatively, in some examples, exterior base layer 92 may underlie at least a portion of wicking layer 110 within moisture capture assembly peripheral region 104 and/or within laterally inward portion 52 of bonded region 50. Additionally or alternatively, in some examples, base layer lateral outward edge 86 of exterior base layer 92 may be aligned with wicking layer lateral edge 112. In other examples, and as schematically illustrated in FIGS. 2-3, base layer lateral outward edge 86 of exterior base layer 92 may be spaced apart from wicking layer lateral edge 112 along laterally inward direction 12 (as illustrated in FIG. 2) or along laterally outward direction 14 (as illustrated in FIGS. 2-3).

In some examples, interior base layer 90 defines a closed region and/or may be described as being a closed structure. That is, interior base layer 90 is continuous around a perimeter region of moisture capture assembly 100, such as generally coinciding with bonded region 50.

In some examples, a configuration of exterior base layer 92 additionally or alternatively may be characterized with reference to moisture barrier layer 132. For example, and as schematically illustrated in FIG. 2, base layer lateral inward edge 84 of exterior base layer 92 may be spaced apart from moisture barrier layer lateral edge 134 along laterally inward direction 12. Additionally or alternatively, in some examples, exterior base layer 92 may underlie at least a portion of moisture barrier layer 132 within moisture capture assembly peripheral region 104, within laterally inward portion 52 of bonded region 50, and/or within laterally outward portion 54 of the bonded region. Additionally or alternatively, and as schematically illustrated FIGS. 2-3 and less schematically illustrated in FIG. 6, in some examples, base layer lateral outward edge 86 of exterior base layer 92 may be aligned with moisture barrier layer lateral edge 134. In other examples, and as schematically illustrated in FIG. 2, base layer lateral outward edge 86 of exterior base layer 92 may be spaced apart from moisture barrier layer lateral edge 134 along laterally inward direction 12 or along laterally outward direction 14.

In some examples, as illustrated in FIG. 3, exterior base layer 92 may be described as being coextensive with the moisture capture assembly and/or as spanning an entirety of reusable absorbent accessory 10. Similarly, in some examples, as illustrated in FIG. 3, moisture barrier layer 132 may be described as being coextensive with exterior base layer 92 and/or as spanning an entirety of reusable absorbent accessory 10.

When present, intermediate base layer 94 may have any suitable position, orientation, and/or extent relative to moisture capture assembly 100, moisture retention portion 120, and/or bonded region 50. In some examples, intermediate base layer 94 and moisture retention portion 120 are directly bonded to one another via a corresponding capture assembly-base bond 64. In particular, in some examples, intermediate base layer 94 is directly bonded to wicking layer 110 and/or to moisture barrier layer 132 (as schematically illustrated in FIG. 2) via respective capture assembly-base bonds 64.

In some examples, and as schematically illustrated in FIG. 2, at least a portion of intermediate base layer 94 underlies at least a portion of moisture capture assembly 100, such as at least a portion of moisture capture assembly peripheral region 104. Stated differently, in some examples, intermediate base layer 94 underlies at least a portion of moisture capture assembly 100 within moisture capture assembly peripheral region 104 and/or within laterally inward portion 52 of bonded region 50.

Additionally or alternatively, in some examples, and as schematically illustrated in FIG. 2, intermediate base layer 94 extends within each of laterally inward portion 52 and laterally outward portion 54 of bonded region 50.

In some examples, and as schematically illustrated in FIG. 2, base layer lateral inward edge 84 of intermediate base layer 94 is spaced apart from moisture retention portion lateral edge 122 along laterally inward direction 12. Additionally or alternatively, in some examples, and as schematically illustrated in FIG. 2, base layer lateral outward edge 86 of intermediate base layer 94 is aligned with moisture capture assembly lateral edge 105 and/or with moisture retention portion lateral edge 122. In other examples, and as schematically illustrated in FIG. 2, base layer lateral outward edge 86 of intermediate base layer 94 is spaced apart from moisture capture assembly lateral edge 105 and/or from moisture retention portion lateral edge 122 along laterally inward direction 12 or along laterally outward direction 14.

In some examples, a configuration of intermediate base layer 94 additionally or alternatively may be characterized with reference to wicking layer 110. For example, and as schematically illustrated in FIG. 2, base layer lateral inward edge 84 of intermediate base layer 94 may be spaced apart from wicking layer lateral edge 112 along laterally inward direction 12. Additionally or alternatively, in some examples, intermediate base layer 94 may underlie at least a portion of wicking layer 110 within moisture capture assembly peripheral region 104 and/or within laterally inward portion 52 of bonded region 50. Additionally or alternatively, in some examples, base layer lateral outward edge 86 of intermediate base layer 94 may be aligned with wicking layer lateral edge 112. In other examples, and as schematically illustrated in FIG. 2, base layer lateral outward edge 86 of intermediate base layer 94 may be spaced apart from wicking layer lateral edge 112 along laterally inward direction 12 or along laterally outward direction 14.

In some examples, a configuration of intermediate base layer 94 additionally or alternatively may be characterized with reference to moisture barrier layer 132. For example, and as schematically illustrated in FIG. 2, base layer lateral inward edge 84 of intermediate base layer 94 may be spaced apart from moisture barrier layer lateral edge 134 along laterally inward direction 12. Additionally or alternatively, in some examples, intermediate base layer 94 may underlie at least a portion of moisture barrier layer 132 within moisture capture assembly peripheral region 104, within laterally inward portion 52 of bonded region 50, and/or within laterally outward portion 54 of the bonded region. Additionally or alternatively, in some examples, base layer lateral outward edge 86 of intermediate base layer 94 may be aligned with moisture barrier layer lateral edge 134. In other examples, and as schematically illustrated in FIG. 2, base layer lateral outward edge 86 of intermediate base layer 94 may be spaced apart from moisture barrier layer lateral edge 134 along laterally inward direction 12 or along laterally outward direction 14.

In examples in which reusable absorbent accessory 10 includes a plurality of base layers 82 that are bonded to one another, the base layers may be bonded to one another in any of a variety of manners. In particular, in various examples, and as schematically illustrated in FIG. 2, two or more of interior base layer 90, exterior base layer 92, and/or intermediate base layer 94 are bonded to one another via corresponding base internal bonds 68. In some examples, at least one base internal bond 68 is positioned only in laterally inward portion 52 of bonded region. Additionally or alternatively, at least one base internal bond 68 may be positioned only in laterally outward portion 54 of bonded region 50. Additionally or alternatively, at least one base internal bond 68 may extend within each of laterally inward portion 52 and laterally outward portion 54 of bonded region 50. In particular, FIG. 3 schematically illustrates an example in which base internal bond 68 that bonds exterior base layer 92 and intermediate base layer 94 to one another extends within each of laterally inward portion 52 and laterally outward portion 54.

In examples in which the plurality of base layers 82 includes interior base layer 90 and intermediate base layer 94, the interior base layer and the intermediate base layer may have any suitable relative orientation. As examples, base layer lateral inward edge 84 of interior base layer 90 may be aligned with base layer lateral inward edge 84 of intermediate base layer 94, or may be spaced apart from the base layer lateral inward edge of the intermediate base layer. More specifically, the base layer lateral inward edge of the interior base layer may be spaced apart from the base layer lateral inward edge of the intermediate base layer along laterally inward direction 12 or along laterally outward direction 14. As additional examples, base layer lateral outward edge 86 of interior base layer 90 may be aligned with base layer lateral outward edge 86 of intermediate base layer 94, or may be spaced apart from the base layer lateral outward edge of the intermediate base layer. More specifically, the base layer lateral outward edge of the interior base layer may be spaced apart from the base layer lateral outward edge of the intermediate base layer along laterally inward direction 12 or along laterally outward direction 14. In some examples, interior base layer 90 and intermediate base layer 94 are directly bonded to one another via a corresponding base internal bond 68.

In examples in which the plurality of base layers 82 includes interior base layer 90 and exterior base layer 92, the interior base layer and the exterior base layer may have any suitable relative orientation. As an example, and as schematically illustrated in FIGS. 2-3 and less schematically illustrated in FIG. 6, base layer lateral outward edge 86 of interior base layer 90 may be aligned with base layer lateral outward edge 86 of exterior base layer 92. In other examples, and as schematically illustrated in FIG. 2, base layer lateral outward edge 86 of interior base layer 90 may be spaced apart from base layer lateral outward edge 86 of exterior base layer 92. More specifically, the base layer lateral outward edge of the interior base layer may be spaced apart from the base layer lateral outward edge of the exterior base layer along laterally inward direction 12 or along laterally outward direction 14. In some examples, interior base layer 90 and exterior base layer 92 are directly bonded to one another via a corresponding base internal bond 68. In other examples, interior base layer 90 and exterior base layer 92 are operatively coupled to one another only via intermediate base layer 94 and/or at least a portion of moisture capture assembly 100. Specifically, in some examples, and as schematically illustrated in FIG. 3, the plurality of base layers 82 includes interior base layer 90 and exterior base layer 92 that are operatively coupled to one another only via one or more layers of moisture capture assembly 100. In particular, FIG. 3 schematically illustrates an example in which the plurality of base layers 82 includes interior base layer 90 and exterior base layer 92 that are separated by moisture barrier layer 132. Accordingly, in such an example, the plurality of adhesive bonds 60 does not include base internal bond 68.

In examples in which the plurality of base layers 82 includes exterior base layer 92 and intermediate base layer 94, the exterior base layer and the intermediate base layer may have any suitable relative orientation. As examples, base layer lateral outward edge 86 of exterior base layer 92 may be aligned with base layer lateral outward edge 86 of intermediate base layer 94, or may be spaced apart from the base layer lateral outward edge of the intermediate base layer. More specifically, the base layer lateral outward edge of the exterior base layer may be spaced apart from the base layer lateral outward edge of the intermediate base layer along laterally inward direction 12 or along laterally outward direction 14. In some examples, exterior base layer 92 and intermediate base layer 94 are directly bonded to one another via a corresponding base internal bond 68.

Turning more specifically to example reusable absorbent accessory 11 illustrated in FIGS. 4-6, example reusable absorbent accessory 11 represents an example of reusable absorbent accessory 10 in the form of a reusable menstrual pad, such as may be worn in conjunction with a separate garment such as a panty. In particular, FIGS. 4-5 illustrate various aspects of the outer surfaces of example reusable absorbent accessory 11, while FIG. 5 is a cross-sectional view illustrating the configurations of base layers 82 and of the components of moisture capture assembly 100 within bonded region 50 and/or within moisture capture assembly peripheral region 104. FIG. 3 is a schematic representation of the configuration illustrated in FIG. 6. As discussed, it is to be understood that the configuration illustrated in FIGS. 3 and 6 may be exhibited at any of a variety of locations along moisture capture assembly peripheral region 104. For example, the configuration illustrated in FIGS. 3 and 6 may be representative of every location along moisture capture assembly peripheral region 104, or may be representative of only a portion of the moisture capture assembly peripheral region.

Turning more specifically to the cross-sectional views of FIGS. 3 and 6, moisture retention portion 120 of example reusable absorbent accessory 11 includes wicking layer 110, first moisture retention layer 126, and second moisture retention layer 128 bonded to one another via corresponding capture assembly internal bonds 66. Specifically, in this example, wicking layer 110 is bonded to first moisture retention layer 126 via a corresponding capture assembly internal bond 66 that extends from a location that is aligned with base layer lateral inward edge 84 of interior base layer 90 to wicking layer lateral edge 112. In this example, wicking layer lateral edge 112 is aligned with moisture retention portion lateral edge 122. Additionally, in this example, first moisture retention layer 126 is bonded to second moisture retention layer 128 via a corresponding capture assembly internal bond 66 that extends to moisture retention portion lateral edge 122.

As illustrated in FIGS. 3 and 6, anti-leak portion 130 of example reusable absorbent accessory 11 includes moisture barrier layer 132 in the form of a moisture-impermeable film that is bonded to moisture retention portion 120. Specifically, in this example, moisture barrier layer 132 is bonded to second moisture retention layer 128 via a corresponding capture assembly internal bond 66 that extends to moisture retention portion lateral edge 122. In this example, moisture barrier layer 132 itself extends beyond moisture retention portion lateral edge 122 and to reusable absorbent accessory lateral edge 28, such that moisture barrier layer lateral edge 134 is spaced apart from moisture retention portion lateral edge 122 along laterally outward direction 14. Thus, in this example, moisture barrier layer 132 represents the portion of moisture capture assembly 100 with the greatest extent in laterally outward direction 14, such that moisture barrier layer lateral edge 134 represents moisture capture assembly lateral edge 105.

As illustrated in FIGS. 3 and 6, reusable absorbent accessory base 80 of example reusable absorbent accessory 11 includes interior base layer 90 and exterior base layer 92. In particular, in this example, interior base layer 90 is bonded to wicking layer 110 via internal peripheral bond 56, which takes the form of a corresponding capture assembly-base bond 64 such that base layer lateral inward edge 84 of interior base layer 90 is spaced apart from wicking layer lateral edge 112 along laterally inward direction 12. In this manner, in this example, interior base layer 90 overlies moisture retention portion 120 within moisture capture assembly peripheral region 104. Additionally, in this example, exterior base layer 92 spans a full width of moisture capture assembly 100 and underlies the moisture capture assembly within moisture capture assembly central region 102 and within moisture capture assembly peripheral region 104. In this example, exterior base layer 92 is bonded to moisture barrier layer 132 via external peripheral bond 58, which takes the form of a corresponding capture assembly-base bond 64 that extends from a point spaced apart from moisture retention portion lateral edge 122 along laterally inward direction 12 to reusable absorbent accessory lateral edge 28.

As illustrated in FIGS. 3 and 6, each of interior base layer 90 and exterior base layer 92 of example reusable absorbent accessory 11 extend along laterally outward direction 14 to reusable absorbent accessory lateral edge 28. In this manner, the respective base layer lateral outward edge 86 of each of interior base layer 90 and exterior base layer 92 is spaced apart from moisture retention portion lateral edge 122 along laterally outward direction 14. Additionally, in this example, each of interior base layer 90 and exterior base layer 92 is directly bonded to moisture barrier layer 132 within laterally outward portion 54 of bonded region 50 via a corresponding capture assembly-base bond 64 that extends to reusable absorbent accessory lateral edge 28.

As further illustrated in FIGS. 4-5, example reusable absorbent accessory 11 includes a pair of wing extensions 30, each of which includes a respective reusable absorbent accessory attachment feature 38. Specifically, in the example of FIGS. 4-5, reusable absorbent accessory attachment features 38 consist of reusable absorbent accessory attachment fasteners 39 that collectively form a hook mechanism for securing wing extensions 30 around the separate garment.

Figure 7:
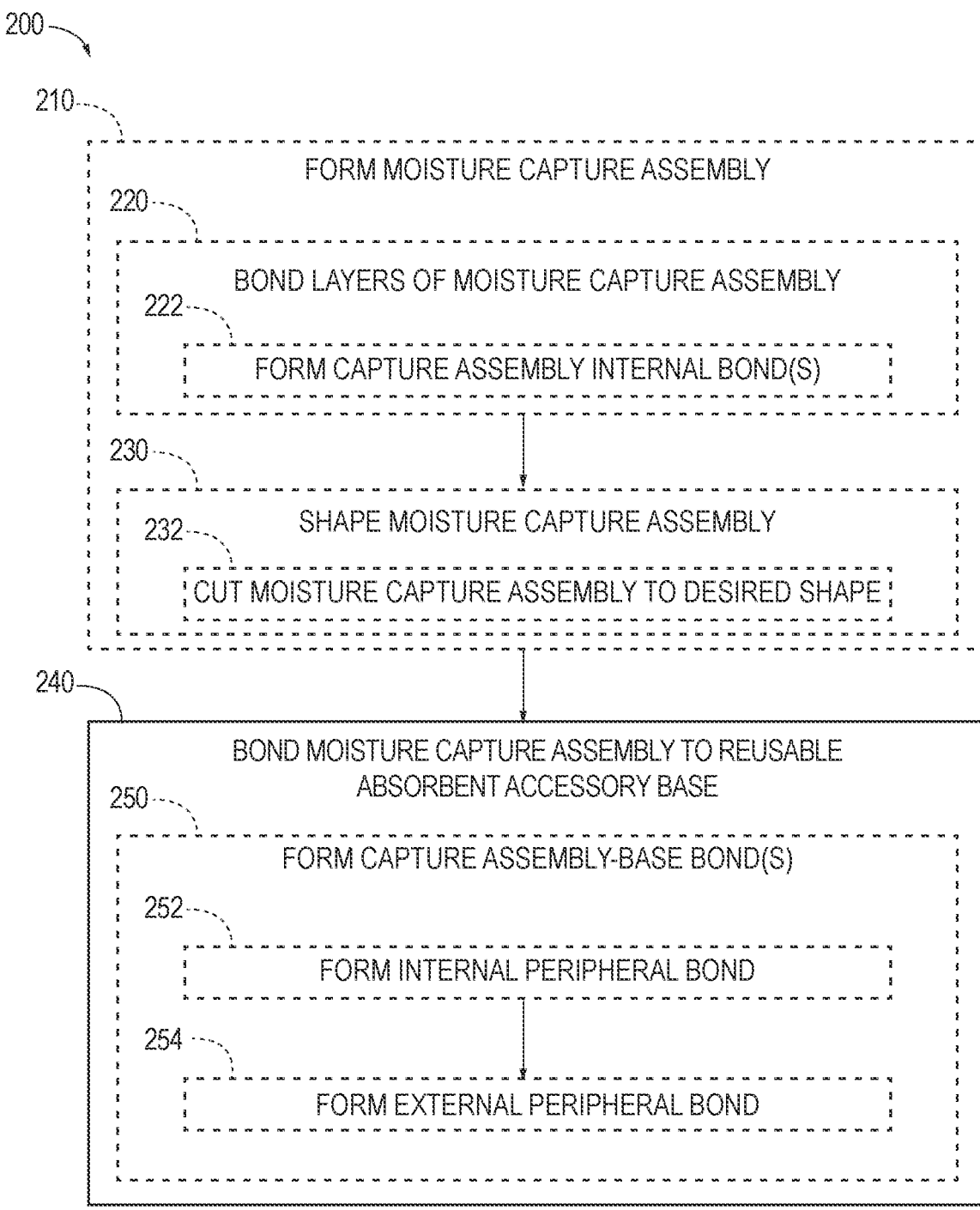
FIG. 7 is a flowchart depicting examples of methods of manufacturing a reusable absorbent accessory according to the present disclosure.

FIG. 7 is a flowchart depicting a method 200, according to the present disclosure, of manufacturing a reusable absorbent accessory, such as reusable absorbent accessory 10 disclosed herein. As shown in FIG. 7, method 200 includes bonding, at 240, a moisture capture assembly to a reusable absorbent accessory base. Examples of moisture capture assemblies and/or of reusable absorbent accessory bases that may be utilized in conjunction with methods 200 are disclosed herein with reference to moisture capture assembly 100 and/or reusable absorbent accessory base 80, respectively.

The bonding the moisture capture assembly to the reusable absorbent accessory base at 240 may be performed in any suitable manner according to the present disclosure. In particular, in some examples, and as shown in FIG. 7, the bonding the moisture capture assembly to the reusable absorbent accessory base at 240 includes forming, at 250, one or more capture assembly-base bonds to bond at least one base layer of the reusable absorbent accessory base and at least a portion of the moisture capture assembly to one another. In particular, in various examples, the bonding the moisture capture assembly to the reusable absorbent accessory base at 240 includes bonding the moisture capture assembly to the reusable absorbent accessory base using an adhesive bond (such as any suitable adhesive bond 60 disclosed herein) and/or without stitching and/or sewing. More specifically, in some examples, and as shown in FIG. 7, the forming the one or more capture assembly-base bonds at 250 includes forming, at 252, an internal peripheral bond and/or forming, at 254, an external peripheral bond. Examples of capture assembly-base bonds, of internal peripheral bonds, of external peripheral bonds, and/or of base layers that may be utilized in conjunction with methods 200 are disclosed herein with reference to capture assembly-base bond 64, internal peripheral bond 56, external peripheral bond 58, and/or any suitable base layer 82, respectively.

In some examples, the bonding the moisture capture assembly to the reusable absorbent accessory base at 240 includes bonding a pre-formed moisture capture assembly to the reusable absorbent accessory base. More specifically, in some examples, and as shown in FIG. 7, method 200 further includes, prior to the bonding the moisture capture assembly to the reusable absorbent accessory base at 240, forming, at 210, the moisture capture assembly.

The forming the moisture capture assembly at 210 may be performed in any suitable manner according to the present disclosure. In particular, in some examples, and as shown in FIG. 7, the forming the moisture capture assembly at 210 includes bonding, at 220, two or more layers of the moisture capture assembly to one another. More specifically, in some examples, the bonding the two or more layers of the moisture capture assembly to one another at 220 may include bonding two or more of a moisture retention portion, an anti-leak portion, one or more moisture retention layers, a first moisture retention layer, a second moisture retention layer, a wicking layer, and/or a moisture barrier layer to one another. In some examples, and as shown in FIG. 7, the forming the moisture capture assembly at 210 and/or the bonding the two or more layers of the moisture capture assembly to one another at 220 includes forming, at 222, one or more capture assembly internal bonds. Examples of moisture retention portions, of anti-leak portions, of moisture retention layers, of first moisture retention layers, of second moisture retention layers, of wicking layers, of moisture barrier layers, and/or of capture assembly internal bonds that may be utilized in conjunction with methods 200 are disclosed herein with reference to moisture retention portion 120, anti-leak portion 130, moisture retention layer 124, first moisture retention layer 126, second moisture retention layer 128, wicking layer 110, moisture barrier layer 132, and/or capture assembly internal bond 66, respectively.

Additionally or alternatively, in some examples, and as shown in FIG. 7, the forming the moisture capture assembly at 210 includes shaping, at 230, the moisture capture assembly, such as to adapt the moisture capture assembly for incorporation with the reusable absorbent accessory base. In some examples, the shaping the moisture capture assembly at 230 is performed subsequent to the bonding the two or more layers of the moisture capture assembly to one another at 220. The shaping the moisture capture assembly at 230 may be performed in any of a variety of manners. As an example, and as shown in FIG. 7, the shaping the moisture capture assembly at 230 may include cutting, at 232, the moisture capture assembly to a desired shape, such as a shape corresponding to that of the reusable absorbent accessory base. More specifically, in some such examples, the cutting the moisture capture assembly to the desired shape at 232 includes utilizing a die cutting process.

Illustrative, non-exclusive examples of inventive subject matter according to the present disclosure are described in the following enumerated paragraphs:

A1. A reusable absorbent accessory configured to be worn by a wearer, the reusable absorbent accessory comprising:
a bonded region;
a reusable absorbent accessory base; and
a moisture capture assembly bonded to the reusable absorbent accessory base within the bonded region;
wherein the moisture capture assembly includes:
an assembly interior side that faces the wearer when the reusable absorbent accessory is worn by the wearer;
an assembly exterior side that faces away from the wearer when the reusable absorbent accessory is worn by the wearer;
a moisture retention portion configured to absorb and retain moisture from the wearer; and
an anti-leak portion configured to restrict moisture from exiting the moisture retention portion; and
wherein the moisture capture assembly is bonded to the reusable absorbent accessory base with a plurality of adhesive bonds formed within the bonded region.

A2. The reusable absorbent accessory of paragraph A1, wherein the plurality of adhesive bonds includes:
an internal peripheral bond positioned on an interior side of at least a portion of the moisture capture assembly; and
an external peripheral bond positioned on an exterior side of at least a portion of the moisture capture assembly.

A3. The reusable absorbent accessory of any of paragraphs A1-A2, wherein the plurality of adhesive bonds includes one or more capture assembly-base bonds; and wherein each capture assembly-base bond of the one or more capture assembly-base bonds operates to bond at least a portion of the moisture capture assembly to at least a portion of the reusable absorbent accessory base.

A4. The reusable absorbent accessory of paragraph A3, wherein the one or more capture assembly-base bonds includes one or both of an/the internal peripheral bond and an/the external peripheral bond.

A5. The reusable absorbent accessory of any of paragraphs A1-A4, wherein the plurality of adhesive bonds includes one or more capture assembly internal bonds; and wherein each capture assembly internal bond of the one or more capture assembly internal bonds operates to bond two or more distinct portions of the moisture capture assembly to one another.

A6. The reusable absorbent accessory of any of paragraphs A1-A5, wherein the plurality of adhesive bonds includes one or more base internal bonds; and wherein each base internal bond of the one or more base internal bonds operates to bond two or more distinct portions of the reusable absorbent accessory base to one another.

A7. The reusable absorbent accessory of paragraph A6, wherein the one or more base internal bonds includes one or both of an/the internal peripheral bond and an/the external peripheral bond.

A8. The reusable absorbent accessory of any of paragraphs A1-A7, wherein one or more adhesive bonds of the plurality of adhesive bonds are formed by an adhesive material that is applied to one or both of the reusable absorbent accessory base and the moisture capture assembly.

A9. The reusable absorbent accessory of paragraph A8, wherein the adhesive material includes one or more of a tape, an elastic tape, a film, an elastic film, a spray-on adhesive, and a thermoset adhesive.

A10. The reusable absorbent accessory of any of paragraphs A8-A9, wherein the adhesive material is one or more of water-resistant, water-repellent, and waterproof.

A11. The reusable absorbent accessory of any of paragraphs A1-A10, wherein one or more adhesive bonds of the plurality of adhesive bonds are formed at least partially via a thermocompression process.

A12. The reusable absorbent accessory of any of paragraphs A1-A11, wherein the reusable absorbent accessory includes a reusable absorbent accessory interior surface that faces the wearer when the reusable absorbent accessory is worn by the wearer and a reusable absorbent accessory exterior surface that faces away from the wearer when the reusable absorbent accessory is worn by the wearer.

A13. The reusable absorbent accessory of paragraph AU, wherein at least a portion of the reusable absorbent accessory interior surface is configured to directly contact the wearer when the reusable absorbent accessory is worn by the wearer.

A14. The reusable absorbent accessory of any of paragraphs A12-A13, wherein the reusable absorbent accessory is configured such that, when the reusable absorbent accessory is worn by the wearer, no portion of the reusable absorbent accessory is positioned directly between the reusable absorbent accessory interior surface and the wearer.

A15. The reusable absorbent accessory of any of paragraphs A12-A14, wherein the reusable absorbent accessory is configured such that, when the reusable absorbent accessory is worn by the wearer, no portion of the reusable absorbent accessory is positioned distal the wearer relative to the reusable absorbent accessory exterior surface.

A16. The reusable absorbent accessory of any of paragraphs A1-A15, wherein the moisture capture assembly includes a moisture capture assembly central region and a moisture capture assembly peripheral region that circumferentially encloses the moisture capture assembly central region; and wherein the bonded region includes at least a portion of the moisture capture assembly peripheral region.

A17. The reusable absorbent accessory of any of paragraphs A1-A16, wherein the bonded region extends at least substantially or fully around a perimeter of a/the moisture capture assembly peripheral region.

A18. The reusable absorbent accessory of any of paragraphs A1-A17, wherein the reusable absorbent accessory base defines a reusable absorbent accessory lateral edge of the reusable absorbent accessory.

A19. The reusable absorbent accessory of paragraph A18, wherein the bonded region extends from a/the moisture capture assembly peripheral region toward, and optionally fully to, the reusable absorbent accessory lateral edge.

A20. The reusable absorbent accessory of any of paragraphs A18-A19, wherein a portion of the moisture capture assembly extends fully to the reusable absorbent accessory lateral edge.

A21. The reusable absorbent accessory of any of paragraphs A18-A19, wherein the moisture capture assembly includes and terminates at a moisture capture assembly lateral edge; optionally wherein the moisture capture assembly lateral edge defines the reusable absorbent accessory lateral edge or wherein the moisture capture assembly lateral edge does not define the reusable absorbent accessory lateral edge.

A22. The reusable absorbent accessory of any of paragraphs A18-A21, wherein the bonded region extends from a/the moisture capture assembly peripheral region to a point that is spaced apart from the reusable absorbent accessory lateral edge; and/or wherein the moisture capture assembly and the bonded region are spaced away from the reusable absorbent accessory lateral edge; and/or wherein the moisture capture assembly and the bonded region do not extend to the reusable absorbent accessory lateral edge.

A23. The reusable absorbent accessory of any of paragraphs A1-A22, wherein the moisture retention portion includes and terminates at a moisture retention portion lateral edge; and wherein the bonded region includes:
  a laterally inward portion that extends from the moisture retention portion lateral edge toward a/the moisture capture assembly central region along a/the laterally inward direction; and
  a laterally outward portion that extends from the moisture retention portion lateral edge away from the moisture retention portion along a laterally outward direction that is opposite the laterally inward direction.

A24. The reusable absorbent accessory of any of paragraphs A1-A23, wherein the moisture capture assembly includes and terminates at a/the moisture capture assembly lateral edge; and wherein one of:
  (i) the moisture capture assembly lateral edge is spaced apart from a/the moisture retention portion lateral edge along a/the laterally outward direction; or
  (ii) the moisture retention portion lateral edge defines the moisture capture assembly lateral edge.

A25. The reusable absorbent accessory of any of paragraphs A1-A24, wherein the reusable absorbent accessory base includes one or more base layers.

A26. The reusable absorbent accessory of paragraph A25, wherein at least one base layer of the one or more base layers and at least a portion of the moisture capture assembly are bonded to one another via at least one capture assembly-base bond of a/the one or more capture assembly-base bonds.

A27. The reusable absorbent accessory of paragraph A26, wherein the capture assembly-base bond is positioned only in a/the laterally inward portion of the bonded region.

A28. The reusable absorbent accessory of paragraph A26, wherein the capture assembly-base bond is positioned only in a/the laterally outward portion of the bonded region.

A29. The reusable absorbent accessory of paragraph A26, wherein the capture assembly-base bond extends within each of a/the laterally inward portion and a/the laterally outward portion of the bonded region.

A30. The reusable absorbent accessory of any of paragraphs A26-A29, wherein the capture assembly-base bond directly bonds the at least one base layer to the assembly interior side of the moisture capture assembly.

A31. The reusable absorbent accessory of any of paragraphs A26-A30, wherein the capture assembly-base bond directly bonds the at least one base layer to the assembly exterior side of the moisture capture assembly.

A32. The reusable absorbent accessory of any of paragraphs A25-A31, wherein each base layer of the one or more base layers includes and terminates at one or both of:
  (i) a base layer lateral inward edge, such that the base layer extends away from the base layer lateral inward edge along a/the laterally outward direction; and
  (ii) a base layer lateral outward edge, such that the base layer extends away from the base layer lateral outward edge along a/the laterally inward direction.

A33. The reusable absorbent accessory of any of paragraphs A25-A31, wherein the one or more base layers includes an interior base layer that forms at least a portion of a/the reusable absorbent accessory interior surface.

A34. The reusable absorbent accessory of paragraph A33, wherein a/the base layer lateral inward edge of the interior base layer is spaced apart from a/the moisture retention portion lateral edge along a/the laterally inward direction.

A35. The reusable absorbent accessory of any of paragraphs A33-A34, wherein at least a portion of the interior base layer overlies at least a portion of the moisture capture assembly; optionally wherein at least a portion of the interior base layer overlies at least a portion of a/the moisture capture assembly peripheral region.

A36. The reusable absorbent accessory of any of paragraphs A33-A35, wherein a/the base layer lateral outward edge of the interior base layer is spaced apart from a/the moisture retention portion lateral edge along a/the laterally outward direction.

A37. The reusable absorbent accessory of any of paragraphs A33-A36, wherein the interior base layer extends within each of a/the laterally inward portion of the bonded region and a/the laterally outward portion of the bonded region.

A38. The reusable absorbent accessory of any of paragraphs A25-A37, wherein the one or more base layers includes an exterior base layer that forms at least a portion of a/the reusable absorbent accessory exterior surface.

A39. The reusable absorbent accessory of paragraph A38, wherein at least a portion of the exterior base layer underlies at least a portion of the moisture capture assembly; optionally wherein at least a portion of the exterior base layer underlies at least a portion of a/the moisture capture assembly peripheral region.

A40. The reusable absorbent accessory of paragraph A39, wherein at least a portion of the exterior base layer underlies at least a portion of a/the moisture capture assembly central region.

A41. The reusable absorbent accessory of any of paragraphs A38-A40, wherein a/the base layer lateral outward edge of the exterior base layer is spaced apart from a/the moisture retention portion lateral edge along a/the laterally outward direction.

A42. The reusable absorbent accessory of any of paragraphs A38-A41, wherein a/the base layer lateral outward edge of the exterior base layer is spaced apart from a/the moisture capture assembly lateral edge along a/the laterally outward direction.

A43. The reusable absorbent accessory of any of paragraphs A38-A42, wherein the exterior base layer extends within each of a/the laterally inward portion of the bonded region and a/the laterally outward portion of the bonded region.

A44. The reusable absorbent accessory of any of paragraphs A25-A43, wherein the one or more base layers includes an intermediate base layer that is positioned at least partially between one or both of:
  (i) one other base layer of the one or more base layers and the moisture capture assembly; and
  two other base layers of the one or more base layers.

A45. The reusable absorbent accessory of paragraph A44, wherein a/the base layer lateral inward edge of the intermediate base layer is spaced apart from a/the moisture retention portion lateral edge along a/the laterally inward direction.

A46. The reusable absorbent accessory of any of paragraphs A44-A45, wherein at least a portion of the intermediate base layer underlies at least a portion of the moisture capture assembly; optionally wherein at least a portion of the intermediate base layer underlies at least a portion of a/the moisture capture assembly peripheral region.

A47. The reusable absorbent accessory of any of paragraphs A44-A46, wherein a/the base layer lateral outward edge of the intermediate base layer is spaced apart from a/the moisture retention portion lateral edge along a/the laterally outward direction.

A48. The reusable absorbent accessory of any of paragraphs A44-A47, wherein a/the base layer lateral outward edge of the intermediate base layer is spaced apart from a/the moisture capture assembly lateral edge along a/the laterally outward direction.

A49. The reusable absorbent accessory of any of paragraphs A44-A48, wherein the intermediate base layer extends within each of a/the laterally inward portion of the bonded region and a/the laterally outward portion of the bonded region.

A50. The reusable absorbent accessory of any of paragraphs A1-A49, wherein two or more of an/the interior base layer, an/the exterior base layer, and an/the intermediate base layer are bonded to one another via a/the base internal bond.

A51. The reusable absorbent accessory of paragraph A50, wherein the base internal bond is positioned only in a/the laterally inward portion of the bonded region.

A52. The reusable absorbent accessory of paragraph A50, wherein the base internal bond is positioned only in a/the laterally outward portion of the bonded region.

A53. The reusable absorbent accessory of paragraph A50, wherein the base internal bond extends within each of a/the laterally inward portion and a/the laterally outward portion of the bonded region.

A54. The reusable absorbent accessory of any of paragraphs A25-A53, wherein the one or more base layers includes an/the interior base layer and an/the intermediate base layer; and wherein a/the base layer lateral inward edge of the interior base layer is aligned with the base layer lateral inward edge of the intermediate base layer.

A55. The reusable absorbent accessory of any of paragraphs A25-A54, wherein the one or more base layers includes an/the interior base layer and an/the intermediate base layer; and wherein a/the base layer lateral inward edge of the interior base layer is spaced apart from the base layer lateral inward edge of the intermediate base layer along a/the laterally inward direction.

A56. The reusable absorbent accessory of any of paragraphs A25-A55, wherein the one or more base layers includes an/the interior base layer and an/the intermediate base layer; and wherein a/the base layer lateral inward edge of the interior base layer is spaced apart from the base layer lateral inward edge of the intermediate base layer along a/the laterally outward direction.

A57. The reusable absorbent accessory of any of paragraphs A25-A56, wherein the one or more base layers includes an/the interior base layer and an/the intermediate base layer; and wherein a/the base layer lateral outward edge of the interior base layer is aligned with the base layer lateral outward edge of the intermediate base layer.

A58. The reusable absorbent accessory of any of paragraphs A25-A57, wherein the one or more base layers includes an/the interior base layer and an/the intermediate base layer; and wherein a/the base layer lateral outward edge of the interior base layer is spaced apart from the base layer lateral outward edge of the intermediate base layer along a/the laterally inward direction.

A59. The reusable absorbent accessory of any of paragraphs A25-A58, wherein the one or more base layers includes an/the interior base layer and an/the intermediate base layer; and wherein a/the base layer lateral outward edge of the interior base layer is spaced apart from the base layer lateral outward edge of the intermediate base layer along a/the laterally outward direction.

A60. The reusable absorbent accessory of any of paragraphs A25-A59, wherein the one or more base layers includes an/the interior base layer and an/the intermediate base layer; and wherein the interior base layer and the intermediate base layer are directly bonded to one another via a/the base internal bond.

A61. The reusable absorbent accessory of any of paragraphs A25-A60, wherein the one or more base layers includes an/the interior base layer and an/the exterior base layer; and wherein a/the base layer lateral outward edge of the interior base layer is aligned with the base layer lateral outward edge of the exterior base layer.

A62. The reusable absorbent accessory of any of paragraphs A25-A61, wherein the one or more base layers includes an/the interior base layer and an/the exterior base layer; and wherein a/the base layer lateral outward edge of the interior base layer is spaced apart from the base layer lateral outward edge of the exterior base layer along a/the laterally inward direction.

A63. The reusable absorbent accessory of any of paragraphs A25-A62, wherein the one or more base layers includes an/the interior base layer and an/the exterior base layer; and wherein a/the base layer lateral outward edge of the interior base layer is spaced apart from the base layer lateral outward edge of the exterior base layer along a/the laterally outward direction.

A64. The reusable absorbent accessory of any of paragraphs A25-A63, wherein the one or more base layers includes an/the interior base layer and an/the intermediate base layer; and wherein the interior base layer and the exterior base layer are directly bonded to one another via a/the base internal bond.

A65. The reusable absorbent accessory of any of paragraphs A25-A64, wherein the one or more base layers includes an/the exterior base layer and an/the intermediate base layer; and wherein a/the base layer lateral outward edge of the exterior base layer is aligned with the base layer lateral outward edge of the intermediate base layer.

A66. The reusable absorbent accessory of any of paragraphs A25-A65, wherein the one or more base layers includes an/the exterior base layer and an/the intermediate base layer; and wherein a/the base layer lateral outward edge of the exterior base layer is spaced apart from the base layer lateral outward edge of the intermediate base layer along a/the laterally inward direction.

A67. The reusable absorbent accessory of any of paragraphs A25-A66, wherein the one or more base layers includes an/the exterior base layer and an/the intermediate base layer; and wherein a/the base layer lateral outward edge of the exterior base layer is spaced apart from the base layer lateral outward edge of the intermediate base layer along a/the laterally outward direction.

A68. The reusable absorbent accessory of any of paragraphs A25-A67, wherein the one or more base layers includes an/the exterior base layer and an/the intermediate base layer; and wherein the exterior base layer and the intermediate base layer are directly bonded to one another via a/the base internal bond.

A69. The reusable absorbent accessory of any of paragraphs A1-A68, wherein the moisture retention portion includes one or more moisture retention layers.

A70. The reusable absorbent accessory of paragraph A69, wherein the one or more moisture retention layers includes a first moisture retention layer and a second moisture retention layer.

A71. The reusable absorbent accessory of paragraph A70, wherein each of the first moisture retention layer and the second moisture retention layer extends to a/the moisture retention portion lateral edge.

A72. The reusable absorbent accessory of any of paragraphs A70-A71, wherein the first moisture retention layer and the second moisture retention layer are operatively coupled to one another.

A73. The reusable absorbent accessory of paragraph A72, wherein the first moisture retention layer and the second moisture retention layer are bonded to one another via at least one of a/the one or more capture assembly internal bonds.

A74. The reusable absorbent accessory of paragraph A73, wherein the capture assembly internal bond is positioned only in a/the laterally inward portion of the bonded region.

A75. The reusable absorbent accessory of paragraph A73, wherein the capture assembly internal bond extends within each of a/the laterally inward portion and a/the laterally outward portion of the bonded region.

A76. The reusable absorbent accessory of any of paragraphs A70-A75, wherein the first moisture retention layer and the second moisture retention layer are at least partially formed of different materials.

A77. The reusable absorbent accessory of any of paragraphs A1-A76, wherein the moisture retention portion includes a wicking layer configured to wick moisture away from the wearer.

A78. The reusable absorbent accessory of paragraph A77, wherein the wicking layer extends within each of a/the moisture capture assembly central region and a/the moisture capture assembly peripheral region.

A79. The reusable absorbent accessory of any of paragraphs A77-A78, wherein the wicking layer includes and terminates at a wicking layer lateral edge.

A80. The reusable absorbent accessory of paragraph A79, wherein the wicking layer lateral edge is aligned with a/the moisture retention portion lateral edge.

A81. The reusable absorbent accessory of paragraph A79, wherein the wicking layer lateral edge is spaced apart from a/the moisture retention portion lateral edge along a/the laterally inward direction.

A82. The reusable absorbent accessory of paragraph A79, wherein the wicking layer lateral edge is spaced apart from a/the moisture retention portion lateral edge along a/the laterally outward direction.

A83. The reusable absorbent accessory of any of paragraphs A79-A82, wherein the wicking layer extends within each of a/the laterally inward portion of the bonded region and a/the laterally outward portion of the bonded region.

A84. The reusable absorbent accessory of any of paragraphs A79-A83, wherein the wicking layer lateral edge defines a/the moisture capture assembly lateral edge.

A85. The reusable absorbent accessory of any of paragraphs A79-A83, wherein the wicking layer lateral edge is spaced apart from a/the moisture capture assembly lateral edge along a/the laterally inward direction.

A86. The reusable absorbent accessory of any of paragraphs A77-A85, wherein the wicking layer is operatively coupled to the moisture retention portion; optionally to the first moisture retention layer.

A87. The reusable absorbent accessory of paragraph A86, wherein the wicking layer and the moisture retention portion are bonded to one another via at least one adhesive bond of the plurality of adhesive bonds; optionally via at least one capture assembly internal bond of a/the one or more capture assembly internal bonds.

A88. The reusable absorbent accessory of any of paragraphs A1-A87, wherein the anti-leak portion includes, and optionally is, a moisture barrier layer that is operatively coupled to the moisture retention portion.

A89. The reusable absorbent accessory of paragraph A88, wherein the moisture barrier layer is bonded to the moisture retention portion via at least one adhesive bond of the plurality of adhesive bonds; optionally via at least one capture assembly internal bond of a/the one or more capture assembly internal bonds.

A90. The reusable absorbent accessory of any of paragraphs A88-A89, wherein the moisture barrier layer includes and terminates at a moisture barrier layer lateral edge.

A91. The reusable absorbent accessory of paragraph A90, wherein the moisture barrier layer lateral edge is aligned with a/the moisture retention portion lateral edge.

A92. The reusable absorbent accessory of paragraph A90, wherein the moisture barrier layer lateral edge is spaced apart from a/the moisture retention portion lateral edge along a/the laterally inward direction.

A93. The reusable absorbent accessory of paragraph A90, wherein the moisture barrier layer lateral edge is spaced apart from a/the moisture retention portion lateral edge along a/the laterally outward direction.

A94. The reusable absorbent accessory of any of paragraphs A88-A93, wherein the moisture barrier layer extends within each of a/the laterally inward portion of the bonded region and a/the laterally outward portion of the bonded region.

A95. The reusable absorbent accessory of any of paragraphs A88-A94, wherein a/the moisture barrier layer lateral edge defines one or both of a/the moisture capture assembly lateral edge and a/the reusable absorbent accessory lateral edge.

A96. The reusable absorbent accessory of any of paragraphs A88-A94, wherein a/the moisture barrier layer lateral edge is spaced apart from a/the moisture capture assembly lateral edge along a/the laterally inward direction.

A97. The reusable absorbent accessory of any of paragraphs A1-A96, wherein the anti-leak portion includes, and optionally is, one or both of a moisture barrier treatment and a moisture barrier film that is applied to the moisture retention portion.

A98. The reusable absorbent accessory of any of paragraphs A1-A97, wherein at least one adhesive bond of the plurality of adhesive bonds is each of a/the capture assembly-base bond and a/the capture assembly internal bond.

A99. The reusable absorbent accessory of any of paragraphs A1-A98, wherein at least one adhesive bond of the plurality of adhesive bonds is each of a/the capture assembly-base bond and a/the base internal bond.

A100. The reusable absorbent accessory of any of paragraphs A1-A99, wherein at least one adhesive bond of the plurality of adhesive bonds is each of a/the capture assembly internal bond and a/the base internal bond.

A101. The reusable absorbent accessory of any of paragraphs A1-A100, wherein a/the one or more base layers includes an/the interior base layer; and wherein the interior base layer and the moisture retention portion are directly bonded to one another via a/the capture assembly-base bond.

A102. The reusable absorbent accessory of any of paragraphs A1-A101, wherein a/the one or more base layers includes an/the interior base layer; and wherein a/the base layer lateral inward edge of the interior base layer is spaced apart from a/the moisture capture assembly lateral edge along a/the laterally inward direction.

A103. The reusable absorbent accessory of any of paragraphs A1-A102, wherein a/the one or more base layers includes an/the interior base layer; and wherein the interior base layer overlies at least a portion of the moisture capture assembly within one or both of a/the moisture capture assembly peripheral region and a/the laterally inward portion of the bonded region.

A104. The reusable absorbent accessory of any of paragraphs A1-A103, wherein a/the one or more base layers includes an/the interior base layer; and wherein a/the base layer lateral outward edge of the interior base layer is aligned with a/the moisture capture assembly lateral edge.

A105. The reusable absorbent accessory of any of paragraphs A1-A104, wherein a/the one or more base layers includes an/the interior base layer; and wherein a/the base layer lateral outward edge of the interior base layer is spaced apart from a/the moisture capture assembly lateral edge along a/the laterally inward direction.

A106. The reusable absorbent accessory of any of paragraphs A1-A105, wherein a/the one or more base layers includes an/the interior base layer; and wherein a/the base layer lateral outward edge of the interior base layer is spaced apart from a/the moisture capture assembly lateral edge along a/the laterally outward direction.

A107. The reusable absorbent accessory of any of paragraphs A1-A106, wherein a/the one or more base layers includes an/the interior base layer; wherein the moisture retention portion includes a/the wicking layer; and wherein the interior base layer and the wicking layer are directly bonded to one another via a/the capture assembly-base bond.

A108. The reusable absorbent accessory of any of paragraphs A1-A107, wherein a/the one or more base layers includes an/the interior base layer; wherein the moisture retention portion includes a/the wicking layer; and wherein a/the base layer lateral inward edge of the interior base layer is spaced apart from a/the wicking layer lateral edge along a/the laterally inward direction.

A109. The reusable absorbent accessory of any of paragraphs A1-A108, wherein a/the one or more base layers includes an/the interior base layer; wherein the moisture retention portion includes a/the wicking layer; and wherein the interior base layer overlies at least a portion of the wicking layer within one or both of a/the moisture capture assembly peripheral region and a/the laterally inward portion of the bonded region.

A110. The reusable absorbent accessory of any of paragraphs A1-A109, wherein a/the one or more base layers includes an/the interior base layer; wherein the moisture retention portion includes a/the wicking layer; and wherein a/the base layer lateral outward edge of the interior base layer is aligned with a/the wicking layer lateral edge.

A111. The reusable absorbent accessory of any of paragraphs A1-A110, wherein a/the one or more base layers includes an/the interior base layer; wherein the moisture retention portion includes a/the wicking layer; and wherein a/the base layer lateral outward edge of the interior base layer is spaced apart from a/the wicking layer lateral edge along a/the laterally outward direction.

A112. The reusable absorbent accessory of any of paragraphs A1-A111, wherein a/the one or more base layers includes an/the interior base layer; wherein the anti-leak portion includes a/the moisture barrier layer; and wherein the interior base layer and the moisture barrier layer are directly bonded to one another via a/the capture assembly-base bond.

A113. The reusable absorbent accessory of any of paragraphs A1-A112, wherein a/the one or more base layers includes an/the interior base layer; wherein the anti-leak portion includes a/the moisture barrier layer; and wherein a/the base layer lateral inward edge of the interior base layer is spaced apart from a/the moisture barrier layer lateral edge along a/the laterally inward direction.

A114. The reusable absorbent accessory of any of paragraphs A1-A113, wherein a/the one or more base layers includes an/the interior base layer; wherein the anti-leak portion includes a/the moisture barrier layer; and wherein the interior base layer overlies at least a portion of the moisture barrier layer within one or both of a/the moisture capture assembly peripheral region and a/the laterally inward portion of the bonded region.

A115. The reusable absorbent accessory of any of paragraphs A1-A114, wherein a/the one or more base layers includes an/the interior base layer; wherein the anti-leak portion includes a/the moisture barrier layer; and wherein the interior base layer overlies at least a portion of the moisture barrier layer within a/the laterally outward portion of the bonded region.

A116. The reusable absorbent accessory of any of paragraphs A1-A115, wherein a/the one or more base layers includes an/the interior base layer; wherein the anti-leak portion includes a/the moisture barrier layer; and wherein a/the base layer lateral outward edge of the interior base layer is aligned with a/the moisture barrier layer lateral edge.

A117. The reusable absorbent accessory of any of paragraphs A1-A116, wherein a/the one or more base layers includes an/the interior base layer; wherein the anti-leak portion includes a/the moisture barrier layer; and wherein a/the base layer lateral outward edge of the interior base layer is spaced apart from a/the moisture barrier layer lateral edge along a/the laterally inward direction.

A118. The reusable absorbent accessory of any of paragraphs A1-A117, wherein a/the one or more base layers includes an/the interior base layer; wherein the anti-leak portion includes a/the moisture barrier layer; and wherein a/the base layer lateral outward edge of the interior base layer is spaced apart from a/the moisture barrier layer lateral edge along a/the laterally outward direction.

A119. The reusable absorbent accessory of any of paragraphs A1-A118, wherein a/the one or more base layers includes an/the intermediate base layer; and wherein the intermediate base layer and the moisture retention portion are directly bonded to one another via a/the capture assembly-base bond.

A120. The reusable absorbent accessory of any of paragraphs A1-A119, wherein a/the one or more base layers includes an/the intermediate base layer; and wherein a/the base layer lateral inward edge of the intermediate base layer is spaced apart from a/the moisture capture assembly lateral edge along a/the laterally inward direction.

A121. The reusable absorbent accessory of any of paragraphs A1-A120, wherein a/the one or more base layers includes an/the intermediate base layer; and wherein the intermediate base layer underlies at least a portion of the moisture capture assembly within one or both of a/the moisture capture assembly peripheral region and a/the laterally inward portion of the bonded region.

A122. The reusable absorbent accessory of any of paragraphs A1-A121, wherein a/the one or more base layers includes an/the intermediate base layer; and wherein a/the base layer lateral outward edge of the intermediate base layer is aligned with a/the moisture capture assembly lateral edge.

A123. The reusable absorbent accessory of any of paragraphs A1-A122, wherein a/the one or more base layers includes an/the intermediate base layer; and wherein a/the base layer lateral outward edge of the intermediate base layer is spaced apart from a/the moisture capture assembly lateral edge along a/the laterally inward direction.

A124. The reusable absorbent accessory of any of paragraphs A1-A123, wherein a/the one or more base layers includes an/the intermediate base layer; and wherein a/the base layer lateral outward edge of the intermediate base layer is spaced apart from a/the moisture capture assembly lateral edge along a/the laterally outward direction.

A125. The reusable absorbent accessory of any of paragraphs A1-A124, wherein a/the one or more base layers includes an/the intermediate base layer; wherein the moisture retention portion includes a/the wicking layer; and wherein the intermediate base layer and the wicking layer are directly bonded to one another via a/the capture assembly-base bond.

A126. The reusable absorbent accessory of any of paragraphs A1-A125, wherein a/the one or more base layers includes an/the intermediate base layer; wherein the moisture retention portion includes a/the wicking layer; and wherein a/the base layer lateral inward edge of the intermediate base layer is spaced apart from a/the wicking layer lateral edge along a/the laterally inward direction.

A127. The reusable absorbent accessory of any of paragraphs A1-A126, wherein a/the one or more base layers includes an/the intermediate base layer; wherein the moisture retention portion includes a/the wicking layer; and wherein the intermediate base layer underlies at least a portion of the wicking layer within one or both of a/the moisture capture assembly peripheral region and a/the laterally inward portion of the bonded region.

A128. The reusable absorbent accessory of any of paragraphs A1-A127, wherein a/the one or more base layers includes an/the intermediate base layer; wherein the moisture retention portion includes a/the wicking layer; and wherein a/the base layer lateral outward edge of the intermediate base layer is aligned with a/the wicking layer lateral edge.

A129. The reusable absorbent accessory of any of paragraphs A1-A128, wherein a/the one or more base layers includes an/the intermediate base layer; wherein the moisture retention portion includes a/the wicking layer; and wherein a/the base layer lateral outward edge of the intermediate base layer is spaced apart from a/the wicking layer lateral edge along a/the laterally inward direction.

A130. The reusable absorbent accessory of any of paragraphs A1-A129, wherein a/the one or more base layers includes an/the intermediate base layer; wherein the moisture retention portion includes a/the wicking layer; and wherein a/the base layer lateral outward edge of the intermediate base layer is spaced apart from a/the wicking layer lateral edge along a/the laterally outward direction.

A131. The reusable absorbent accessory of any of paragraphs A1-A130, wherein a/the one or more base layers includes an/the intermediate base layer; wherein the anti-leak portion includes a/the moisture barrier layer; and wherein the intermediate base layer and the moisture barrier layer are directly bonded to one another via a/the capture assembly-base bond.

A132. The reusable absorbent accessory of any of paragraphs A1-A131, wherein a/the one or more base layers includes an/the intermediate base layer; wherein the anti-leak portion includes a/the moisture barrier layer; and wherein a/the base layer lateral inward edge of the intermediate base layer is spaced apart from a/the moisture barrier layer lateral edge along a/the laterally inward direction.

A133. The reusable absorbent accessory of any of paragraphs A1-A132, wherein a/the one or more base layers includes an/the intermediate base layer; wherein the anti-leak portion includes a/the moisture barrier layer; and wherein the intermediate base layer underlies at least a portion of the moisture barrier layer within one or both of a/the moisture capture assembly peripheral region and a/the laterally inward portion of the bonded region.

A134. The reusable absorbent accessory of any of paragraphs A1-A133, wherein a/the one or more base layers includes an/the intermediate base layer; wherein the anti-leak portion includes a/the moisture barrier layer; and wherein the intermediate base layer underlies at least a portion of the moisture barrier layer within a/the laterally outward portion of the bonded region.

A135. The reusable absorbent accessory of any of paragraphs A1-A134, wherein a/the one or more base layers includes an/the intermediate base layer; wherein the anti-leak portion includes a/the moisture barrier layer; and wherein a/the base layer lateral outward edge of the intermediate base layer is aligned with a/the moisture barrier layer lateral edge.

A136. The reusable absorbent accessory of any of paragraphs A1-A135, wherein a/the one or more base layers includes an/the intermediate base layer; wherein the anti-leak portion includes a/the moisture barrier layer; and wherein a/the base layer lateral outward edge of the intermediate base layer is spaced apart from a/the moisture barrier layer lateral edge along a/the laterally inward direction.

A137. The reusable absorbent accessory of any of paragraphs A1-A136, wherein a/the one or more base layers includes an/the intermediate base layer; wherein the anti-leak portion includes a/the moisture barrier layer; and wherein a/the base layer lateral outward edge of the intermediate base layer is spaced apart from a/the moisture barrier layer lateral edge along a/the laterally outward direction.

A138. The reusable absorbent accessory of any of paragraphs A1-A137, wherein a/the one or more base layers includes an/the exterior base layer; and wherein the exterior base layer and the moisture retention portion are directly bonded to one another via a/the capture assembly-base bond.

A139. The reusable absorbent accessory of any of paragraphs A1-A138, wherein a/the one or more base layers includes an/the exterior base layer; and wherein the exterior base layer underlies at least a portion of the moisture capture assembly within one or both of a/the moisture capture assembly peripheral region and a/the laterally inward portion of the bonded region.

A140. The reusable absorbent accessory of any of paragraphs A1-A139, wherein a/the one or more base layers includes an/the exterior base layer; and wherein a/the base layer lateral outward edge of the exterior base layer is aligned with a/the moisture capture assembly lateral edge.

A141. The reusable absorbent accessory of any of paragraphs A1-A140, wherein a/the one or more base layers includes an/the exterior base layer; and wherein a/the base layer lateral outward edge of the exterior base layer is spaced apart from a/the moisture capture assembly lateral edge along a/the laterally inward direction.

A142. The reusable absorbent accessory of any of paragraphs A1-A141, wherein a/the one or more base layers includes an/the exterior base layer; and wherein a/the base layer lateral outward edge of the exterior base layer is spaced apart from a/the moisture capture assembly lateral edge along a/the laterally outward direction.

A143. The reusable absorbent accessory of any of paragraphs A1-A142, wherein a/the one or more base layers includes an/the exterior base layer; wherein the moisture retention portion includes a/the wicking layer; and wherein the exterior base layer and the wicking layer are directly bonded to one another via a/the capture assembly-base bond.

A144. The reusable absorbent accessory of any of paragraphs A1-A143, wherein a/the one or more base layers includes an/the exterior base layer; wherein the moisture retention portion includes a/the wicking layer; and wherein the exterior base layer underlies at least a portion of the wicking layer within one or both of a/the moisture capture assembly peripheral region and a/the laterally inward portion of the bonded region.

A145. The reusable absorbent accessory of any of paragraphs A1-A144, wherein a/the one or more base layers includes an/the exterior base layer; wherein the moisture retention portion includes a/the wicking layer; and wherein a/the base layer lateral outward edge of the exterior base layer is aligned with a/the wicking layer lateral edge.

A146. The reusable absorbent accessory of any of paragraphs A1-A145, wherein a/the one or more base layers includes an/the exterior base layer; wherein the moisture retention portion includes a/the wicking layer; and wherein a/the base layer lateral outward edge of the exterior base layer is spaced apart from a/the wicking layer lateral edge along a/the laterally inward direction.

A147. The reusable absorbent accessory of any of paragraphs A1-A146, wherein a/the one or more base layers includes an/the exterior base layer; wherein the moisture retention portion includes a/the wicking layer; and wherein a/the base layer lateral outward edge of the exterior base layer is spaced apart from a/the wicking layer lateral edge along a/the laterally outward direction.

A148. The reusable absorbent accessory of any of paragraphs A1-A147, wherein a/the one or more base layers includes an/the exterior base layer; wherein the anti-leak portion includes a/the moisture barrier layer; and wherein the exterior base layer and the moisture barrier layer are directly bonded to one another via a/the capture assembly-base bond.

A149. The reusable absorbent accessory of any of paragraphs A1-A148, wherein a/the one or more base layers includes an/the exterior base layer; wherein the anti-leak portion includes a/the moisture barrier layer; and wherein the exterior base layer underlies at least a portion of the moisture barrier layer within one or both of a/the moisture capture assembly peripheral region and a/the laterally inward portion of the bonded region.

A150. The reusable absorbent accessory of any of paragraphs A1-A149, wherein a/the one or more base layers includes an/the exterior base layer; wherein the anti-leak portion includes a/the moisture barrier layer; and wherein the exterior base layer underlies at least a portion of the moisture barrier layer within a/the laterally outward portion of the bonded region.

A151. The reusable absorbent accessory of any of paragraphs A1-A150, wherein a/the one or more base layers includes an/the exterior base layer; wherein the anti-leak portion includes a/the moisture barrier layer; and wherein a/the base layer lateral outward edge of the exterior base layer is aligned with a/the moisture barrier layer lateral edge.

A152. The reusable absorbent accessory of any of paragraphs A1-A151, wherein a/the one or more base layers includes an/the exterior base layer; wherein the anti-leak portion includes a/the moisture barrier layer; and wherein a/the base layer lateral outward edge of the exterior base layer is spaced apart from a/the moisture barrier layer lateral edge along a/the laterally inward direction.

A153. The reusable absorbent accessory of any of paragraphs A1-A152, wherein a/the one or more base layers includes an/the exterior base layer; wherein the anti-leak portion includes a/the moisture barrier layer; and wherein a/the base layer lateral outward edge of the exterior base layer is spaced apart from a/the moisture barrier layer lateral edge along a/the laterally outward direction.

A154. The reusable absorbent accessory of any of paragraphs A1-A153, wherein one or more of the reusable absorbent accessory base, a/the one or more base layers, an/the interior base layer, an/the exterior base layer, and an/the interior base layer is at least partially formed of one or more of a natural fiber, cotton, a synthetic fiber, polyester, nylon, Spandex™ fabric, and combinations thereof.

A155. The reusable absorbent accessory of any of paragraphs A1-A154, wherein one or more of the moisture capture assembly, a/the moisture retention portion, a/the first moisture retention layer, a/the second moisture retention layer, a/the wicking layer, and a/the moisture barrier layer is at least partially formed of one or more of a natural fiber, cotton, a synthetic fiber, polyester, nylon, Spandex™ fabric, and combinations thereof.

A156. The reusable absorbent accessory of any of paragraphs A1-A155, wherein the reusable absorbent accessory is configured to be utilized in conjunction with a separate garment, optionally with one or both of an undergarment and a panty.

A157. The reusable absorbent accessory of paragraph A156, further comprising one or more wing extensions configured to one or both of engage the separate garment and operatively secure the reusable absorbent accessory relative to the separate garment.

A158. The reusable absorbent accessory of paragraph A157, wherein the one or more wing extensions are configured to at least partially wrap around the separate garment.

A159. The reusable absorbent accessory of any of paragraphs A157-A158, wherein at least one of the one or more wing extensions includes a reusable absorbent accessory attachment feature configured to secure the reusable absorbent accessory relative to the separate garment.

A160. The reusable absorbent accessory of paragraph A159, wherein the reusable absorbent accessory attachment feature includes, and optionally is, a reusable absorbent accessory attachment fastener; and optionally wherein the reusable absorbent accessory attachment fastener is one or more of a hook, a hook receiver, and a hook-and-loop fastener.

A161. The reusable absorbent accessory of any of paragraphs A157-A160, wherein each of the one or more wing extensions defines at least a portion of a/the reusable absorbent accessory lateral edge.

A162. The reusable absorbent accessory of any of paragraphs A1-A161, wherein the reusable absorbent accessory is one or both of a menstrual pad and an incontinence pad.

A163. The reusable absorbent accessory of any of paragraphs A1-A162, A164. The reusable absorbent accessory of any of paragraphs A1-A163, wherein the reusable absorbent accessory is configured to be washed and re-worn numerous times.

B1. A reusable absorbent accessory configured to be worn by a wearer and to be washed and re-worn numerous times, the reusable absorbent accessory comprising:
a plurality of adhesive bonds within a bonded region of the reusable absorbent accessory;

a reusable absorbent accessory base, wherein the reusable absorbent accessory base defines a reusable absorbent accessory lateral edge of the reusable absorbent accessory; and a moisture capture assembly bonded to the reusable absorbent accessory base within the bonded region of the reusable absorbent accessory by at least a subset of the plurality of adhesive bonds, wherein the moisture capture assembly has an assembly interior side that faces the wearer when the reusable absorbent accessory is worn by the wearer and an assembly exterior side that faces away from the wearer when the reusable absorbent accessory is worn by the wearer, and wherein the moisture capture assembly comprises at least:

a moisture retention portion configured to absorb and retain moisture from the wearer; and an anti-leak portion configured to restrict moisture from exiting the moisture retention portion and positioned toward the assembly exterior side of the moisture capture assembly relative to the moisture retention portion;

wherein the reusable absorbent accessory has a perimeter, and wherein the bonded region extends fully around the perimeter of the reusable absorbent accessory.

B2. The reusable absorbent accessory of paragraph B1, wherein the reusable absorbent accessory is configured to be utilized in conjunction with a separate garment, wherein the reusable absorbent accessory further comprises a pair of wing extensions configured to operatively secure the reusable absorbent accessory relative to the separate garment, wherein each of the pair of wing extensions defines at least a portion of the reusable absorbent accessory lateral edge, and wherein the pair of wing extensions are configured to at least partially wrap around the separate garment.

B3. The reusable absorbent accessory of paragraph B2, wherein each of the pair of wing extensions includes an attachment feature configured to secure the reusable absorbent accessory relative to the separate garment.

B4. The reusable absorbent accessory of any of paragraphs B1-B3, wherein the plurality of adhesive bonds comprises:

an internal peripheral bond positioned on the assembly interior side and that operates to bond the moisture capture assembly to the reusable absorbent accessory base; and an external peripheral bond positioned on the assembly exterior side and that operates to bond the moisture capture assembly to the reusable absorbent accessory base.

B5. The reusable absorbent accessory of paragraph B4, wherein the plurality of adhesive bonds further comprises one or more capture assembly internal bonds, and wherein each capture assembly internal bond of the one or more capture assembly internal bonds operates to bond two or more distinct portions of the moisture capture assembly to one another.

B6. The reusable absorbent accessory of paragraph B5, wherein the moisture retention portion includes:

a wicking layer that comprises the assembly interior side and is configured to wick moisture away from the wearer; and one or more moisture retention layers between the wicking layer and the anti-leak portion; and wherein the one or more capture assembly internal bonds operate to bond the wicking layer to a moisture retention layer of the one or more moisture retention layers.

B7. The reusable absorbent accessory of paragraph B6, wherein the one or more moisture retention layers comprises two moisture retention layers positioned between the wicking layer and the anti-leak portion, and wherein the one or more capture assembly internal bonds further operate to bond the two moisture retention layers to one another.

B8. The reusable absorbent accessory of paragraph B7, wherein the two moisture retention layers are formed of different materials.

B9. The reusable absorbent accessory of any of paragraphs B6-B8, wherein the anti-leak portion comprises a moisture barrier layer, and wherein the one or more capture assembly internal bonds further operate to bond the moisture barrier layer to the one or more moisture retention layers.

B10. The reusable absorbent accessory of paragraph B9, wherein the moisture barrier layer comprises a moisture barrier layer lateral edge, wherein the moisture retention portion comprises a moisture retention portion lateral edge, and wherein the moisture barrier layer lateral edge is spaced laterally outward from the moisture retention portion lateral edge.

B11. The reusable absorbent accessory of paragraph B10, wherein the reusable absorbent accessory base comprises an interior base layer and an exterior base layer;

wherein the internal peripheral bond further operates to bond the interior base layer to the wicking layer and to the moisture barrier layer; and wherein the external peripheral bond further operates to bond the exterior base layer to the moisture barrier layer.

B12. The reusable absorbent accessory of paragraph B11, wherein the exterior base layer and the moisture barrier layer are coextensive and span an entirety of the reusable absorbent accessory.

B13. The reusable absorbent accessory of any of paragraphs B10-612, wherein the interior base layer is a closed structure that coincides with the bonded region.

B14. The reusable absorbent accessory of any of paragraphs B6-B13, wherein the anti-leak portion comprises a moisture barrier treatment applied to a moisture retention layer of the one or more moisture retention layers.

B15. The reusable absorbent accessory of any of paragraphs B1-B14, further comprising the subject matter of any of paragraphs A1-A164.

C1. A reusable absorbent accessory configured to be worn by a wearer and to be washed and re-worn numerous times, the reusable absorbent accessory comprising:

a reusable absorbent accessory base comprising an interior base layer and an exterior base layer, wherein the reusable absorbent accessory base defines a reusable absorbent accessory lateral edge of the reusable absorbent accessory;

a moisture capture assembly bonded to the reusable absorbent accessory base within a bonded region of the reusable absorbent accessory, wherein the moisture capture assembly has an assembly interior side that faces the wearer when the reusable absorbent accessory is worn by the wearer and an assembly exterior side that faces away from the wearer when the reusable absorbent accessory is worn by the wearer, and wherein the moisture capture assembly comprises at least:

a wicking layer that comprises the assembly interior side and is configured to wick moisture away from the wearer;

a moisture retention portion configured to absorb and retain moisture from the wearer and comprising one or more moisture retention layers, wherein the moisture retention portion comprises a moisture retention portion lateral edge; and a moisture barrier layer configured to restrict moisture from exiting the moisture retention portion, wherein the one or more moisture retention layers are positioned between the wicking layer and the moisture barrier layer, and wherein the moisture barrier layer comprises a moisture barrier layer lateral edge that is spaced laterally outward from the moisture retention portion lateral edge; and a plurality of adhesive bonds within the bonded region of the reusable absorbent accessory, wherein the plurality of adhesive bonds comprises:

an internal peripheral bond positioned on the assembly interior side and that operates to bond the moisture capture assembly to the reusable absorbent accessory base, and to bond the interior base layer to the wicking layer and to the moisture barrier layer;

an external peripheral bond positioned on the assembly exterior side and that operates to bond the exterior base layer to the moisture barrier layer; and one or more capture assembly internal bonds that operate to bond the wicking layer to the one or more moisture retention layers, and to bond the moisture barrier layer to the one or more moisture retention layers;

wherein the interior base layer is a closed structure that coincides with the bonded region.

C2. The reusable absorbent accessory of paragraph C1, wherein the exterior base layer spans an entirety of the reusable absorbent accessory.

C3. The reusable absorbent accessory of paragraph C2, wherein the exterior base layer and the moisture barrier layer are coextensive with one another.

C4. The reusable absorbent accessory of any of paragraphs C1-C3, wherein the one or more moisture retention layers comprises two moisture retention layers positioned between the wicking layer and the moisture barrier layer, and wherein the one or more capture assembly internal bonds further operate to bond the two moisture retention layers to one another.

C5. The reusable absorbent accessory of any of paragraphs C1-C4, further comprising the subject matter of any of paragraphs A1-A164.

D1. A method of manufacturing the reusable absorbent accessory of any of paragraphs A1-A5, the method comprising:

bonding, with the plurality of adhesive bonds, the moisture capture assembly to the reusable absorbent accessory base.

D2. The method of paragraph D1, wherein the bonding the moisture capture assembly to the reusable absorbent accessory base includes forming a/the one or more capture assembly-base bonds to bond at least one base layer of a/the one or more base layers and at least a portion of the moisture capture assembly to one another.

D3. The method of paragraph D2, wherein the forming the one or more capture assembly-base bonds includes forming an/the internal peripheral bond.

D4. The method of any of paragraphs D2-D3, wherein the forming the one or more capture assembly-base bonds includes forming an/the external peripheral bond.

D5. The method of any of paragraphs D1-D4, further comprising, prior to the bonding the moisture capture assembly to the reusable absorbent accessory base, forming the moisture capture assembly.

D6. The method of paragraph D5, wherein the forming the moisture capture assembly includes bonding two or more layers of the moisture capture assembly to one another; optionally wherein the two or more layers of the moisture capture assembly include two or more of the moisture retention portion, the anti-leak portion, a/the one or more moisture retention layers, a/the first moisture retention layer, a/the second moisture retention layer, a/the wicking layer, and the moisture barrier layer.

D7. The method of any of paragraphs D5-D6, wherein the forming the moisture capture assembly includes forming a/the one or more capture assembly internal bonds.

D8. The method of any of paragraphs D5-D7, wherein the forming the moisture capture assembly includes shaping the moisture capture assembly.

D9. The method of paragraph D8, when dependent from paragraph D6, wherein the shaping the moisture capture assembly is performed subsequent to the bonding the two or more layers of the moisture capture assembly to one another.

D10. The method of any of paragraphs D8-D9, wherein the moisture capture assembly includes cutting the moisture capture assembly to a desired shape.

D11. The method of paragraph D10, wherein the cutting the moisture capture assembly to the desired shape includes die cutting.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the term "and/or" placed between a first entity and a second entity means one of (1) the first entity, (2) the second entity, and (3) the first entity and the second entity. Multiple entries listed with "and/or" should be construed in the same manner, i.e., "one or more" of the entities so conjoined. Other entities optionally may be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one example, to A only (optionally including entities other than B); in another example, to B only (optionally including entities other than A); in yet another example, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

As used herein, the phrase "at least substantially," when modifying a degree or relationship, includes not only the recited "substantial" degree or relationship, but also the full extent of the recited degree or relationship. A substantial amount of a recited degree or relationship may include at least 75% of the recited degree or relationship. For example, a first component that extends at least substantially around a second component includes a first component that extends around at least 75% of a circumference of the second component and also includes a first component that extends fully circumferentially around the second component.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

The various disclosed elements of apparatuses disclosed herein are not required to all apparatuses according to the present disclosure, and the present disclosure includes all novel and non-obvious combinations and subcombinations of the various elements disclosed herein. Moreover, one or more of the various elements disclosed herein may define independent inventive subject matter that is separate and apart from the whole of a disclosed apparatus. Accordingly, such inventive subject matter is not required to be associated with the specific apparatuses that are expressly disclosed herein, and such inventive subject matter may find utility in apparatuses and/or methods that are not expressly disclosed herein.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure or subsequently filed claims recite "a" or "a first" element or the equivalent thereof, such disclosure and/or claims should be understood to include incorporation of one or more such elements, neither requiring nor excluding two or more such elements.

The invention claimed is:

1. A reusable absorbent accessory configured to be worn by a wearer and to be washed and re-worn numerous times, the reusable absorbent accessory comprising:
   a plurality of adhesive bonds within a bonded region of the reusable absorbent accessory;
   a reusable absorbent accessory base, wherein the reusable absorbent accessory base defines a reusable absorbent accessory lateral edge of the reusable absorbent accessory; and
   a moisture capture assembly bonded to the reusable absorbent accessory base within the bonded region of the reusable absorbent accessory by at least a subset of the plurality of adhesive bonds, wherein the moisture capture assembly has an assembly interior side that faces the wearer when the reusable absorbent accessory is worn by the wearer and an assembly exterior side that faces away from the wearer when the reusable absorbent accessory is worn by the wearer, and wherein the moisture capture assembly comprises at least:
      a moisture retention portion configured to absorb and retain moisture from the wearer; and
      an anti-leak portion configured to restrict moisture from exiting the moisture retention portion and positioned toward the assembly exterior side of the moisture capture assembly relative to the moisture retention portion;
   wherein the reusable absorbent accessory has a perimeter, and wherein the bonded region extends fully around the perimeter of the reusable absorbent accessory; and
   wherein the plurality of adhesive bonds comprises:
      an internal peripheral bond positioned on the assembly interior side and that operates to bond the moisture capture assembly to the reusable absorbent accessory base; and
      an external peripheral bond positioned on the assembly exterior side and that operates to bond the moisture capture assembly to the reusable absorbent accessory base.

2. The reusable absorbent accessory of claim 1, wherein the reusable absorbent accessory is configured to be utilized in conjunction with a separate garment, wherein the reusable absorbent accessory further comprises a pair of wing extensions configured to operatively secure the reusable absorbent accessory relative to the separate garment, wherein each of the pair of wing extensions defines at least a portion of the reusable absorbent accessory lateral edge, and wherein the pair of wing extensions are configured to at least partially wrap around the separate garment.

3. The reusable absorbent accessory of claim 2, wherein each of the pair of wing extensions includes an attachment feature configured to secure the reusable absorbent accessory relative to the separate garment.

4. The reusable absorbent accessory of claim 1, wherein the plurality of adhesive bonds further comprises one or more capture assembly internal bonds, and wherein each capture assembly internal bond of the one or more capture assembly internal bonds operates to bond two or more distinct portions of the moisture capture assembly to one another.

5. The reusable absorbent accessory of claim 4,
   wherein the moisture retention portion includes:

a wicking layer that comprises the assembly interior side and is configured to wick moisture away from the wearer; and one or more moisture retention layers between the wicking layer and the anti-leak portion; and wherein the one or more capture assembly internal bonds operate to bond the wicking layer to a moisture retention layer of the one or more moisture retention layers.

6. The reusable absorbent accessory of claim 5, wherein the one or more moisture retention layers comprises two moisture retention layers positioned between the wicking layer and the anti-leak portion, and wherein the one or more capture assembly internal bonds further operate to bond the two moisture retention layers to one another.

7. The reusable absorbent accessory of claim 6, wherein the two moisture retention layers are formed of different materials.

8. The reusable absorbent accessory of claim 5, wherein the anti-leak portion comprises a moisture barrier layer, and wherein the one or more capture assembly internal bonds further operate to bond the moisture barrier layer to the one or more moisture retention layers.

9. The reusable absorbent accessory of claim 8, wherein the moisture barrier layer comprises a moisture barrier layer lateral edge, wherein the moisture retention portion comprises a moisture retention portion lateral edge, and wherein the moisture barrier layer lateral edge is spaced laterally outward from the moisture retention portion lateral edge.

10. The reusable absorbent accessory of claim 9,
wherein the reusable absorbent accessory base comprises an interior base layer and an exterior base layer;
wherein the internal peripheral bond further operates to bond the interior base layer to the wicking layer and to the moisture barrier layer; and
wherein the external peripheral bond further operates to bond the exterior base layer to the moisture barrier layer.

11. The reusable absorbent accessory of claim 10, wherein the exterior base layer and the moisture barrier layer are coextensive and span an entirety of the reusable absorbent accessory.

12. The reusable absorbent accessory of claim 9, wherein the interior base layer is a closed structure that coincides with the bonded region.

13. The reusable absorbent accessory of claim 5, wherein the anti-leak portion comprises a moisture barrier treatment applied to a moisture retention layer of the one or more moisture retention layers.

14. A method of manufacturing the reusable absorbent accessory of claim 1, the method comprising:
bonding, with the plurality of adhesive bonds, the moisture capture assembly to the reusable absorbent accessory base.

15. The reusable absorbent accessory of claim 1, wherein one or more adhesive bonds of the plurality of adhesive bonds are formed by an adhesive material that is applied to one or both of the reusable absorbent accessory base and the moisture capture assembly, and wherein the adhesive material includes one or more of a tape, an elastic tape, a film, an elastic film, a spray-on adhesive, and a thermoset adhesive.

16. A reusable absorbent accessory configured to be worn by a wearer and to be washed and re-worn numerous times, the reusable absorbent accessory comprising:
a reusable absorbent accessory base comprising an interior base layer and an exterior base layer, wherein the reusable absorbent accessory base defines a reusable absorbent accessory lateral edge of the reusable absorbent accessory;
a moisture capture assembly bonded to the reusable absorbent accessory base within a bonded region of the reusable absorbent accessory, wherein the moisture capture assembly has an assembly interior side that faces the wearer when the reusable absorbent accessory is worn by the wearer and an assembly exterior side that faces away from the wearer when the reusable absorbent accessory is worn by the wearer, and wherein the moisture capture assembly comprises at least:
a wicking layer that comprises the assembly interior side and is configured to wick moisture away from the wearer;
a moisture retention portion configured to absorb and retain moisture from the wearer and comprising one or more moisture retention layers, wherein the moisture retention portion comprises a moisture retention portion lateral edge; and
a moisture barrier layer configured to restrict moisture from exiting the moisture retention portion, wherein the one or more moisture retention layers are positioned between the wicking layer and the moisture barrier layer, and wherein the moisture barrier layer comprises a moisture barrier layer lateral edge that is spaced laterally outward from the moisture retention portion lateral edge; and
a plurality of adhesive bonds within the bonded region of the reusable absorbent accessory, wherein the plurality of adhesive bonds comprises:
an internal peripheral bond positioned on the assembly interior side and that operates to bond the moisture capture assembly to the reusable absorbent accessory base, and to bond the interior base layer to the wicking layer and to the moisture barrier layer;
an external peripheral bond positioned on the assembly exterior side and that operates to bond the exterior base layer to the moisture barrier layer; and
one or more capture assembly internal bonds that operate to bond the wicking layer to the one or more moisture retention layers, and to bond the moisture barrier layer to the one or more moisture retention layers;
wherein the interior base layer is a closed structure that coincides with the bonded region.

17. The reusable absorbent accessory of claim 16, wherein the exterior base layer spans an entirety of the reusable absorbent accessory.

18. The reusable absorbent accessory of claim 17, wherein the exterior base layer and the moisture barrier layer are coextensive with one another.

19. The reusable absorbent accessory of claim 16, wherein the one or more moisture retention layers comprises two moisture retention layers positioned between the wicking layer and the moisture barrier layer, and wherein the one or more capture assembly internal bonds further operate to bond the two moisture retention layers to one another.

20. A method of manufacturing the reusable absorbent accessory of claim 16, the method comprising:
bonding, with the plurality of adhesive bonds, the moisture capture assembly to the reusable absorbent accessory base.

* * * * *